(12) United States Patent
Vestgaarden et al.

(10) Patent No.: US 12,409,042 B2
(45) Date of Patent: Sep. 9, 2025

(54) METHOD AND APPARATUS FOR SPINAL FACET FUSION

(71) Applicant: VGI Medical, LLC, Largo, FL (US)

(72) Inventors: Tov Vestgaarden, Madeira Beach, FL (US); Scott Ely, Pinellas Park, FL (US)

(73) Assignee: VGI Medical, LLC, Largo, FL (US)

( * ) Notice: Subject to any disclaimer, the term of this patent is extended or adjusted under 35 U.S.C. 154(b) by 0 days.

(21) Appl. No.: 18/239,206

(22) Filed: Aug. 29, 2023

(65) Prior Publication Data

US 2024/0197490 A1    Jun. 20, 2024

Related U.S. Application Data

(63) Continuation of application No. 16/879,385, filed on May 20, 2020, now Pat. No. 11,737,884, which is a
(Continued)

(51) Int. Cl.
*A61F 2/44* (2006.01)
*A61B 17/16* (2006.01)
(Continued)

(52) U.S. Cl.
CPC .......... *A61F 2/4405* (2013.01); *A61F 2/4611* (2013.01); *A61B 17/1671* (2013.01);
(Continued)

(58) Field of Classification Search
CPC ................. A61F 2/4405; A61F 2/4611; A61F 2002/30266; A61B 17/1671; A61B 17/1757
(Continued)

(56) References Cited

U.S. PATENT DOCUMENTS 3,848,601 A    11/1974 Ma et al.
4,441,492 A    4/1984 Rydell et al.
(Continued)

FOREIGN PATENT DOCUMENTS

WO    WO 2004/043278    5/2004
WO    WO 2008/153732    12/2008
WO    WO 2012/054596    4/2012

OTHER PUBLICATIONS

Extended European Search Report for European European Application No. 12833016 with a mailing date of May 28, 2015; Applicant: Vestgaarden, Tov Inge.
(Continued)

*Primary Examiner* — Eduardo C Robert
*Assistant Examiner* — Tara Rose E Carter
(74) *Attorney, Agent, or Firm* — Pandiscio & Pandiscio

(57) ABSTRACT

A spinal facet fusion implant comprising: an elongated body having a distal end, a proximal end and a longitudinal axis extending between the distal end and the proximal end, the elongated body being characterized by a superior body surface and an inferior body surface; a superior stabilizer extending outwardly from the superior body surface, the superior stabilizer being characterized by a superior stabilizer surface; and an inferior stabilizer extending outwardly from the inferior body surface, the inferior stabilizer being characterized by an inferior stabilizer surface; wherein (i) the superior body surface and the inferior body surface are tapered relative to one another, and/or (ii) the superior stabilizer surface and the inferior stabilizer surface are tapered relative to one another.

21 Claims, 36 Drawing Sheets

Related U.S. Application Data continuation of application No. 15/631,670, filed on Jun. 23, 2017, now abandoned.

(60) Provisional application No. 62/353,809, filed on Jun. 23, 2016.

(51) Int. Cl.
    *A61B 17/17*    (2006.01)
    *A61F 2/30*     (2006.01)
    *A61F 2/46*     (2006.01)

(52) U.S. Cl.
    CPC . *A61B 17/1757* (2013.01); *A61F 2002/30179* (2013.01); *A61F 2002/30266* (2013.01)

(58) Field of Classification Search
    USPC .................. 606/246–249; 623/17.11–17.16
    See application file for complete search history.

(56) References Cited

U.S. PATENT DOCUMENTS

| | | |
|---|---|---|
| 4,501,269 A | 2/1985 | Bagby |
| 5,015,247 A | 5/1991 | Michelson |
| 5,389,080 A | 2/1995 | Yoon |
| 5,484,437 A | 1/1996 | Michelson |
| 5,505,732 A | 4/1996 | Michelson |
| 5,522,899 A | 6/1996 | Michelson |
| 5,569,290 A | 10/1996 | McAfee |
| 5,593,409 A | 1/1997 | Michelson |
| 5,609,635 A | 3/1997 | Michelson |
| 5,609,636 A | 3/1997 | Kohrs et al. |
| 5,683,394 A | 11/1997 | Rinner |
| 5,741,253 A | 4/1998 | Michelson |
| 5,772,661 A | 6/1998 | Michelson |
| 5,776,199 A | 7/1998 | Michelson |
| 5,785,710 A | 7/1998 | Michelson |
| 5,797,909 A | 8/1998 | Michelson |
| 5,860,973 A | 1/1999 | Michelson |
| 6,080,155 A | 6/2000 | Michelson |
| 6,096,038 A | 8/2000 | Michelson |
| 6,113,602 A | 9/2000 | Sand |
| 6,120,502 A | 9/2000 | Michelson |
| 6,123,705 A | 9/2000 | Michelson |
| 6,149,650 A | 11/2000 | Michelson |
| 6,197,033 B1 | 3/2001 | Haid, Jr. et al. |
| 6,200,322 B1 | 3/2001 | Branch et al. |
| 6,206,826 B1 | 3/2001 | Mathews |
| 6,210,412 B1 | 4/2001 | Michelson |
| 6,264,656 B1 | 7/2001 | Michelson |
| 6,270,498 B1 | 8/2001 | Michelson |
| 6,287,313 B1 | 9/2001 | Sasso |
| 6,302,914 B1 | 10/2001 | Michelson |
| 6,402,785 B1 | 6/2002 | Zdeblick et al. |
| 6,436,098 B1 | 8/2002 | Michelson |
| 6,447,544 B1 | 9/2002 | Michelson |
| 6,447,547 B1 | 9/2002 | Michelson |
| 6,478,823 B1 | 11/2002 | Michelson |
| 6,540,747 B1 | 4/2003 | Marino |
| 6,582,432 B1 | 6/2003 | Michelson |
| 6,605,089 B1 | 8/2003 | Michelson |
| 6,648,893 B2 | 11/2003 | Dudasik |
| 6,733,535 B2 | 5/2004 | Michelson |
| 6,758,849 B1 | 7/2004 | Michelson |
| 6,770,074 B2 | 8/2004 | Michelson |
| 6,783,547 B2 | 8/2004 | Castro |
| 6,875,213 B2 | 4/2005 | Michelson |
| 6,923,810 B1 | 8/2005 | Michelson |
| 7,056,321 B2 | 6/2006 | Pagliuca et al. |
| 7,066,961 B2 | 6/2006 | Michelson |
| 7,101,398 B2 | 9/2006 | Dooris et al. |
| 7,115,128 B2 | 10/2006 | Michelson |
| 7,207,991 B2 | 4/2007 | Michelson |
| 7,223,269 B2 | 5/2007 | Chappuis |
| 7,264,622 B2 | 9/2007 | Michelson |
| 7,288,093 B2 | 10/2007 | Michelson |
| 7,326,214 B2 | 2/2008 | Michelson |
| 7,452,369 B2 | 11/2008 | Barry |
| 7,455,672 B2 | 11/2008 | Michelson |
| 7,503,933 B2 | 3/2009 | Michelson |
| 7,517,358 B2 | 4/2009 | Petersen |
| D597,669 S | 8/2009 | Petersen |
| 7,621,938 B2 | 11/2009 | Molz, IV |
| 7,648,509 B2 | 1/2010 | Stark |
| 7,674,296 B2 | 3/2010 | Rhoda et al. |
| 7,691,148 B2 | 4/2010 | Michelson |
| 7,708,761 B2 | 5/2010 | Petersen |
| 7,758,648 B2 | 7/2010 | Castleman et al. |
| D623,298 S | 9/2010 | Thomas et al. |
| 7,850,736 B2 | 12/2010 | Heinz |
| 7,918,891 B1 | 4/2011 | Curran et al. |
| 8,162,981 B2 | 4/2012 | Vestgaarden |
| 8,348,950 B2 | 1/2013 | Assell et al. |
| 8,454,618 B2 | 6/2013 | Stark |
| 8,623,053 B2 | 1/2014 | Vestgaarden |
| 8,808,377 B2 | 8/2014 | Donner |
| 8,882,818 B1 | 11/2014 | Vestgaarden |
| 9,017,407 B2 | 4/2015 | Donner |
| 9,375,243 B1 | 6/2016 | Vestgaarden |
| 9,452,065 B1 | 9/2016 | Lawson |
| 9,883,874 B1 | 2/2018 | Vestgaarden |
| 9,895,176 B2 | 2/2018 | Vestgaarden |
| 2002/0077641 A1 | 6/2002 | Michelson |
| 2002/0082701 A1 | 6/2002 | Zdeblick et al. |
| 2002/0138144 A1 | 9/2002 | Michelson |
| 2002/0198532 A1 | 12/2002 | Michelson |
| 2003/0032962 A1 | 2/2003 | Mcgahan et al. |
| 2003/0135279 A1 | 7/2003 | Michelson |
| 2003/0139816 A1 | 7/2003 | Michelson |
| 2003/0158553 A1 | 8/2003 | Michelson |
| 2004/0059337 A1 | 3/2004 | Hanson et al. |
| 2004/0073217 A1 | 4/2004 | Michelson |
| 2004/0097927 A1 | 5/2004 | Yeung et al. |
| 2004/0133277 A1 | 7/2004 | Michelson |
| 2004/0176853 A1 | 9/2004 | Sennett et al. |
| 2004/0225360 A1 | 11/2004 | Malone |
| 2004/0236331 A1 | 11/2004 | Michelson |
| 2004/0260286 A1* | 12/2004 | Ferree .................. A61F 2/4455 606/247 |
| 2005/0038512 A1 | 2/2005 | Michelson |
| 2005/0065518 A1 | 3/2005 | Michelson |
| 2005/0065519 A1 | 3/2005 | Michelson |
| 2005/0070898 A1 | 3/2005 | Jones |
| 2005/0149030 A1 | 7/2005 | Serhan et al. |
| 2005/0149192 A1 | 7/2005 | Zucherman et al. |
| 2005/0149193 A1 | 7/2005 | Zucherman et al. |
| 2005/0159813 A1 | 7/2005 | Molz, IV |
| 2005/0165399 A1 | 7/2005 | Michelson |
| 2005/0165489 A1 | 7/2005 | Michelson |
| 2006/0004367 A1 | 1/2006 | Alamin et al. |
| 2006/0036247 A1 | 2/2006 | Michelson |
| 2006/0036323 A1 | 2/2006 | Carl et al. |
| 2006/0054171 A1 | 3/2006 | Dall |
| 2006/0058793 A1 | 3/2006 | Michelson |
| 2006/0064099 A1 | 3/2006 | Pavlov et al. |
| 2006/0084992 A1 | 4/2006 | Michelson |
| 2006/0085068 A1 | 4/2006 | Barry |
| 2006/0111779 A1 | 5/2006 | Petersen |
| 2006/0111782 A1 | 5/2006 | Petersen |
| 2006/0142762 A1 | 6/2006 | Michelson |
| 2006/0184172 A1 | 8/2006 | Michelson |
| 2006/0190081 A1 | 8/2006 | Kraus et al. |
| 2006/0200138 A1 | 9/2006 | Michelson |
| 2006/0200139 A1 | 9/2006 | Michelson |
| 2006/0200164 A1 | 9/2006 | Michelson |
| 2006/0235391 A1 | 10/2006 | Sutterlin, III |
| 2006/0241758 A1 | 10/2006 | Peterman et al. |
| 2006/0241764 A1 | 10/2006 | Michelson |
| 2006/0247650 A1 | 11/2006 | Yerby et al. |
| 2006/0259142 A1 | 11/2006 | Dooris et al. |
| 2006/0264953 A1 | 11/2006 | Falahee |
| 2006/0276790 A1 | 12/2006 | Dawson et al. |
| 2007/0010889 A1 | 1/2007 | Francis |

(56) References Cited

U.S. PATENT DOCUMENTS

| | | |
|---|---|---|
| 2007/0050033 A1* | 3/2007 | Reo .................... A61B 17/7062 623/17.13 |
| 2007/0055373 A1 | 3/2007 | Hudgins et al. |
| 2007/0083265 A1 | 4/2007 | Malone |
| 2007/0112428 A1 | 5/2007 | Lancial |
| 2007/0118218 A1 | 5/2007 | Hooper |
| 2007/0118224 A1 | 5/2007 | Shah et al. |
| 2007/0149976 A1 | 6/2007 | Hale et al. |
| 2007/0233107 A1 | 10/2007 | Zielinski |
| 2008/0132949 A1 | 6/2008 | Aferzon et al. |
| 2008/0154305 A1 | 6/2008 | Foley et al. |
| 2008/0154374 A1 | 6/2008 | Labrom |
| 2008/0183211 A1 | 7/2008 | Lamborne et al. |
| 2008/0255666 A1 | 10/2008 | Fisher et al. |
| 2009/0012527 A1 | 1/2009 | Mignucci et al. |
| 2009/0036927 A1 | 2/2009 | Vestgaarden |
| 2009/0062858 A1 | 3/2009 | Dziedzic et al. |
| 2009/0069816 A1 | 3/2009 | Sasing et al. |
| 2009/0076551 A1 | 3/2009 | Petersen |
| 2009/0187247 A1 | 7/2009 | Metcalf, Jr. et al. |
| 2009/0216238 A1 | 8/2009 | Stark |
| 2009/0234389 A1 | 9/2009 | Chuang et al. |
| 2009/0259261 A1 | 10/2009 | Reiley |
| 2010/0076443 A1 | 3/2010 | Bertagnoli et al. |
| 2010/0241166 A1 | 9/2010 | Dwyer et al. |
| 2010/0318127 A1 | 12/2010 | Phan et al. |
| 2010/0324683 A1 | 12/2010 | Reichen et al. |
| 2011/0166600 A1 | 7/2011 | Lamborne et al. |
| 2012/0101582 A1 | 4/2012 | Raiszadeh et al. |
| 2012/0197263 A1 | 8/2012 | Copf et al. |
| 2012/0239089 A1 | 9/2012 | Druma et al. |
| 2012/0271351 A1* | 10/2012 | Vestgaarden ...... A61B 17/7064 606/279 |
| 2013/0282128 A1 | 10/2013 | Mckay |
| 2014/0200668 A1 | 7/2014 | Kirschman |
| 2014/0324103 A1 | 10/2014 | Levieux et al. |
| 2014/0336763 A1 | 11/2014 | Donner et al. |

OTHER PUBLICATIONS

Guiot, B.H. et al., A Minimally Invasive Technique for Decompression of the Lumbar Spine, Spine, vol. 27, No. 4, 2002, pp. 432-438.

International Preliminary Report on Patentability as issued on Apr. 3, 2014 for corresponding International (PCT) Patent Application No. PCT/US2012/056304 with an international filing date of Sep. 20, 2012.

International Search Report and Written Opinion as issued on Feb. 26, 2013 for corresponding International (PCT) Patent Application No. PCT/US2012/056304 with an international filing date of Sep. 20, 2012.

International Search Report with a mailing date of May 24, 2012 pertaining to International (PCT) Patent Application No. PCT/US2011/056878 with an international filing date of Oct. 19, 2011.

Kai, Y. et al., Posterior Lumbar Interbody Fusion Using Local Facet Joint Autograft and Pedicle Screw Fixation, Spine, vol. 29, No. 1, 2003, pp. 41-46.

Mitchell, J., Surgical Treatment of Affections of the Lumbosacral and Sacroiliac Joints, Surgery, vol. 4, Iss. 1, 1938, pp. 33-43.

Park, Y., Facet Fusion in the Lumbosacral Spine: 2-Year Follow-Up Study, Neurosurgery, vol. 51, No. 1, Jul. 2002, pp. 88-96.

Powers, C., Minimally Invasive Fusion and Fixation Techniques, Neurosurgery Clinics of North America, vol. 17, 2006, pp. 477-489.

Stein et al., Percutaneous Facet Joint Fusion: Preliminary Experience, Journal of Vascular and Interventional Radiology, vol. 4, No. 1, Jan. 1993, pp. 69-74.

VGI Medical, LLC, Surgical Technique Guide, 2013.

Whalen, E., The Society of Cardiovascular and Interventional Radiology: 17th Annual Scientific Meeting, American Journal of Roentgenology, vol. 159, 1992, pp. 639-645.

* cited by examiner

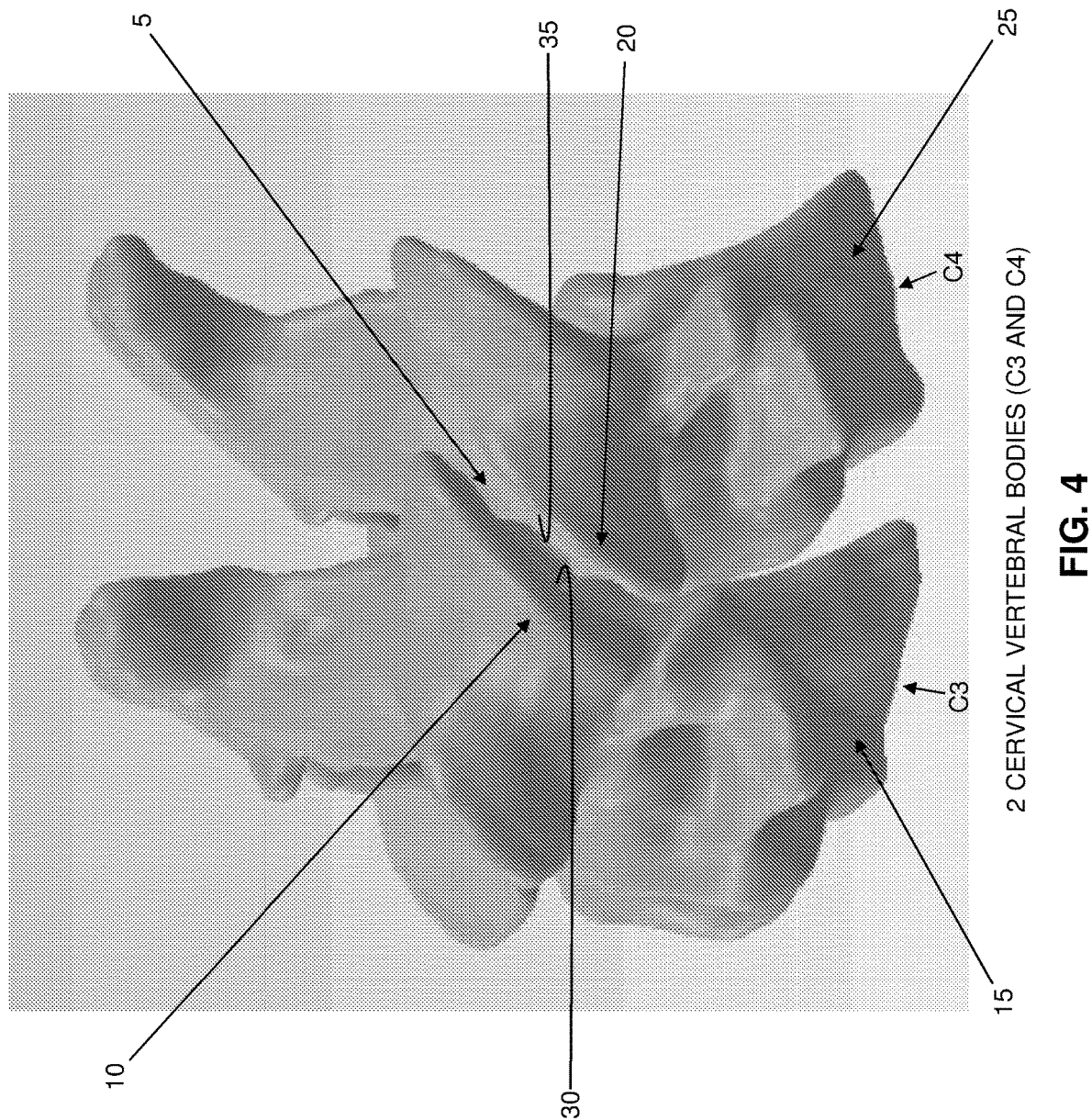

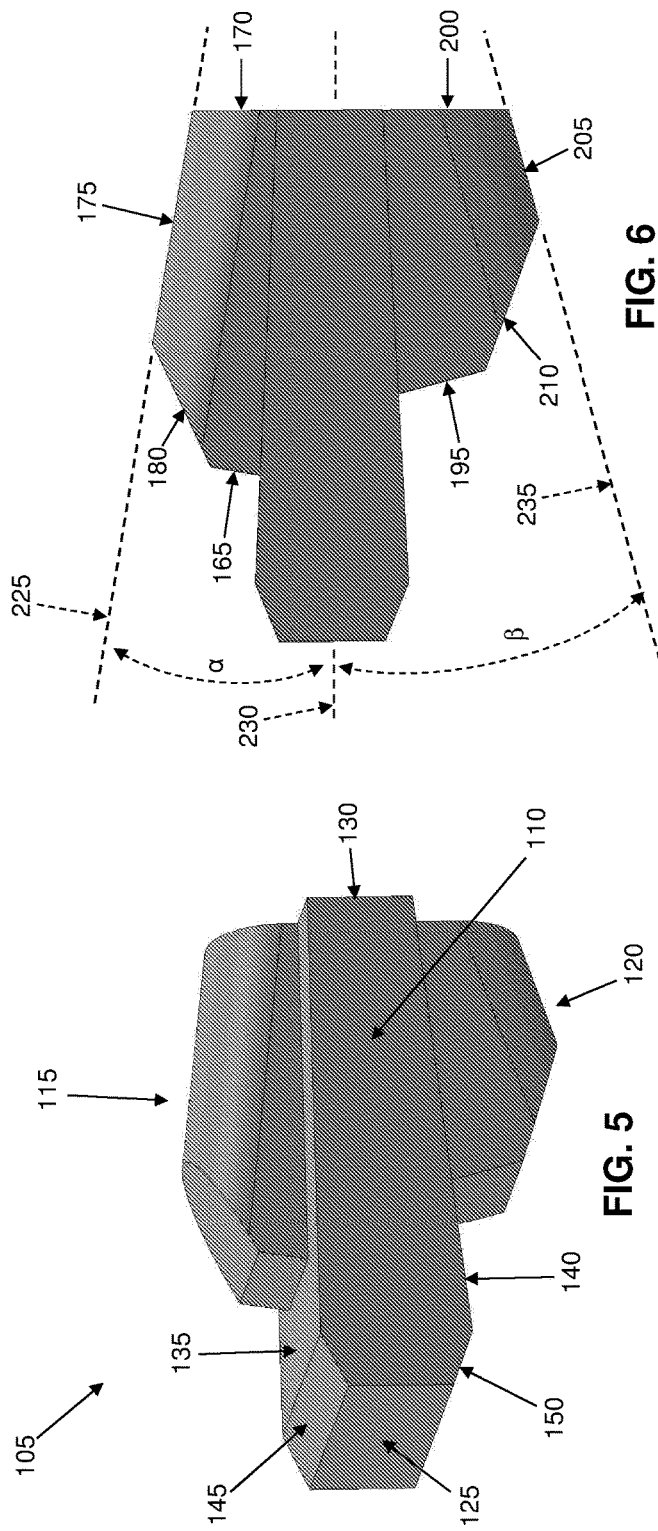
FIG. 6
FIG. 5
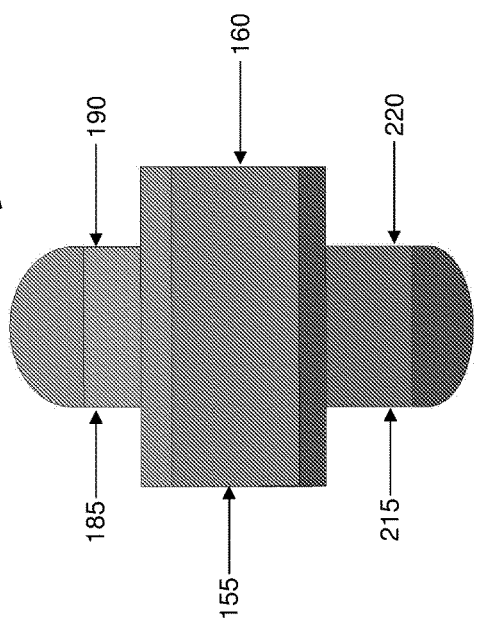
FIG. 7

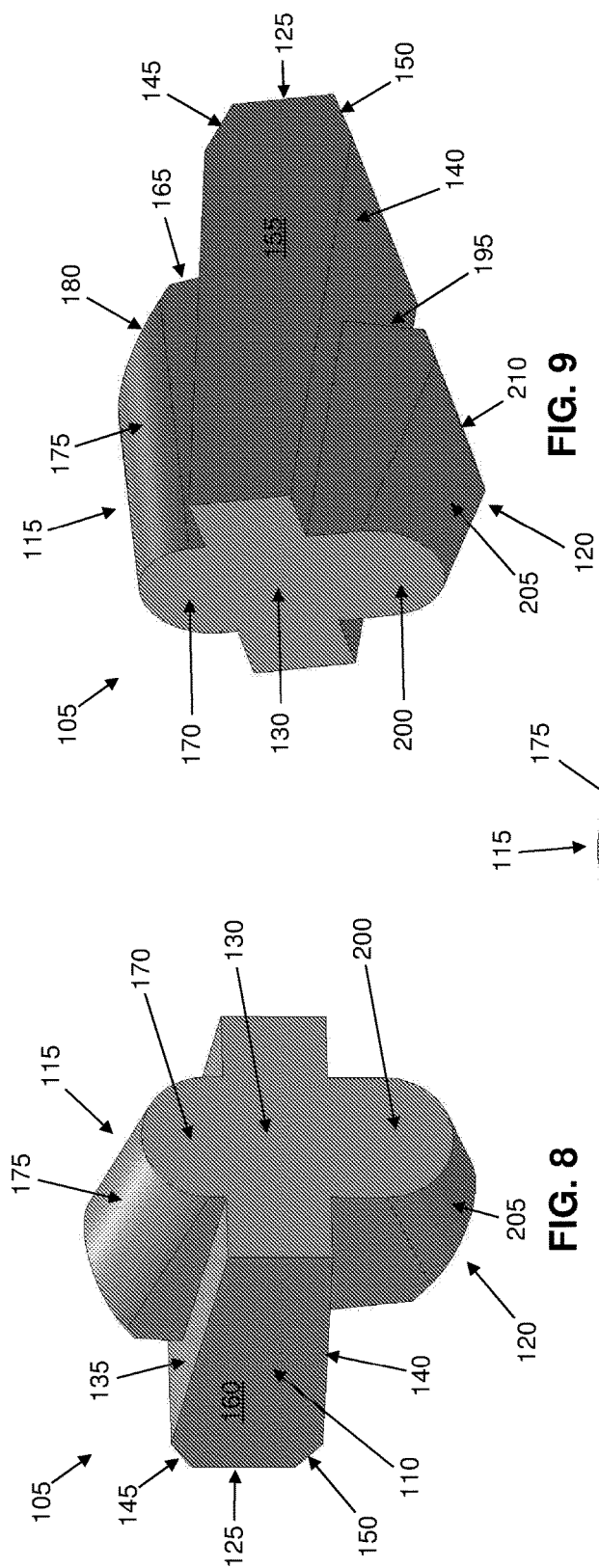
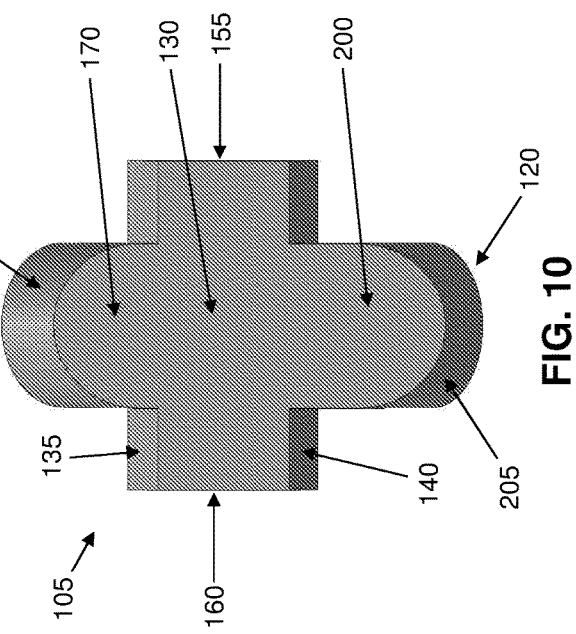
FIG. 8
FIG. 9
FIG. 10

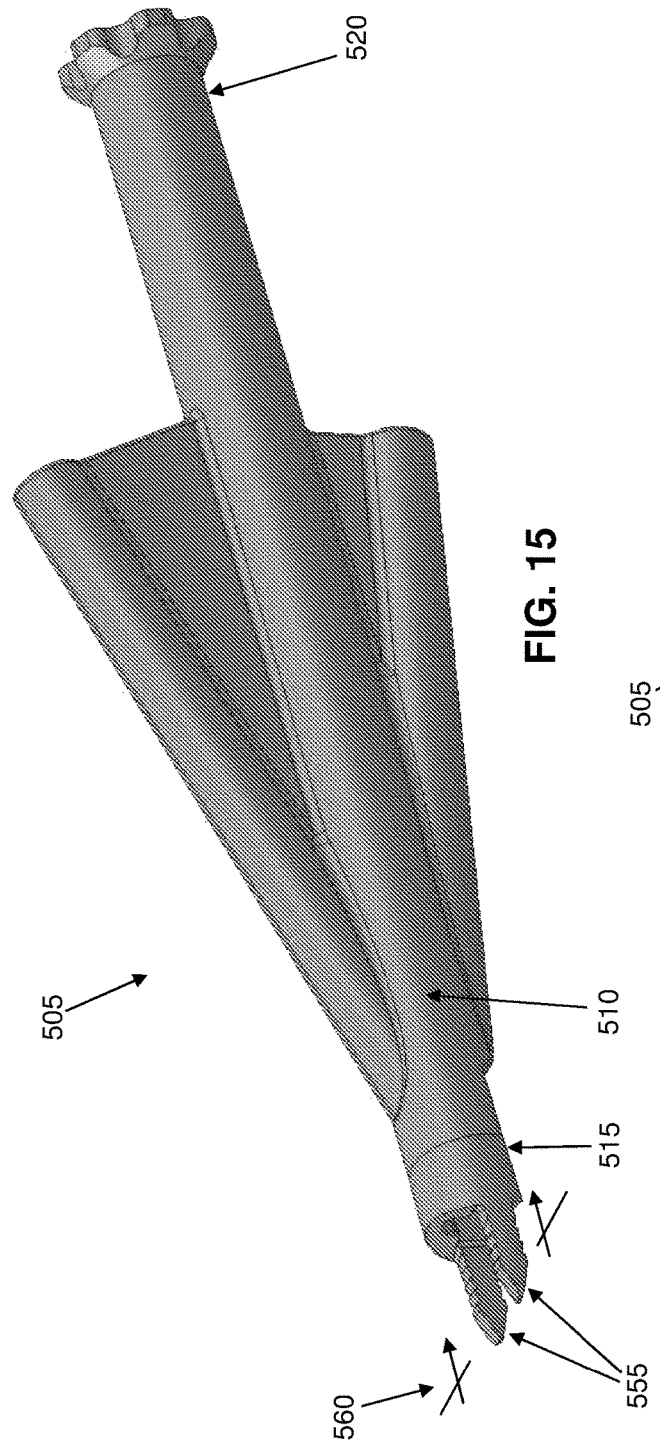
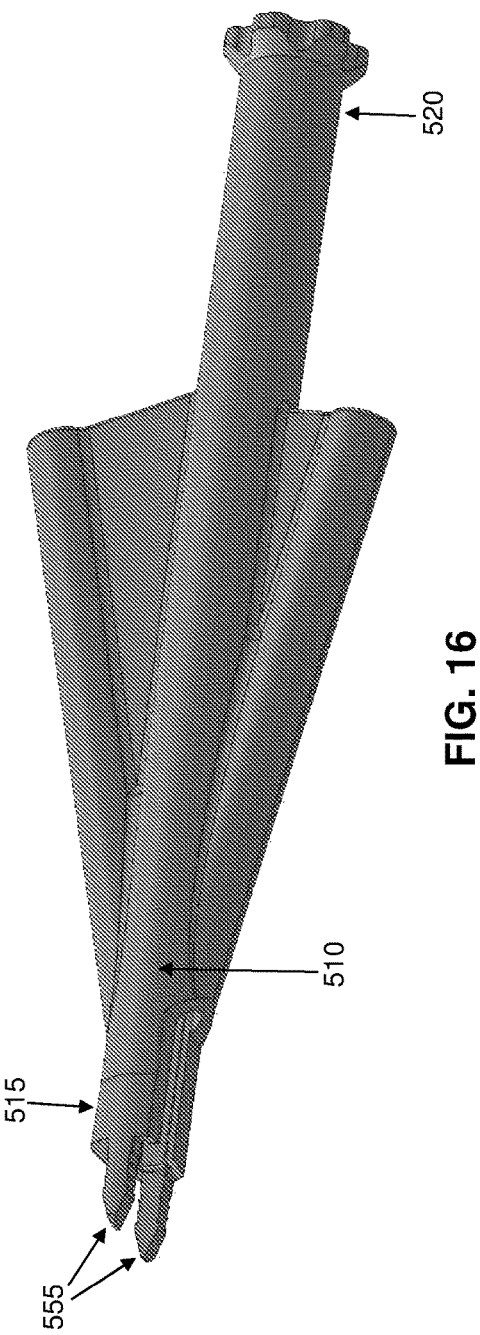
FIG. 15
FIG. 16

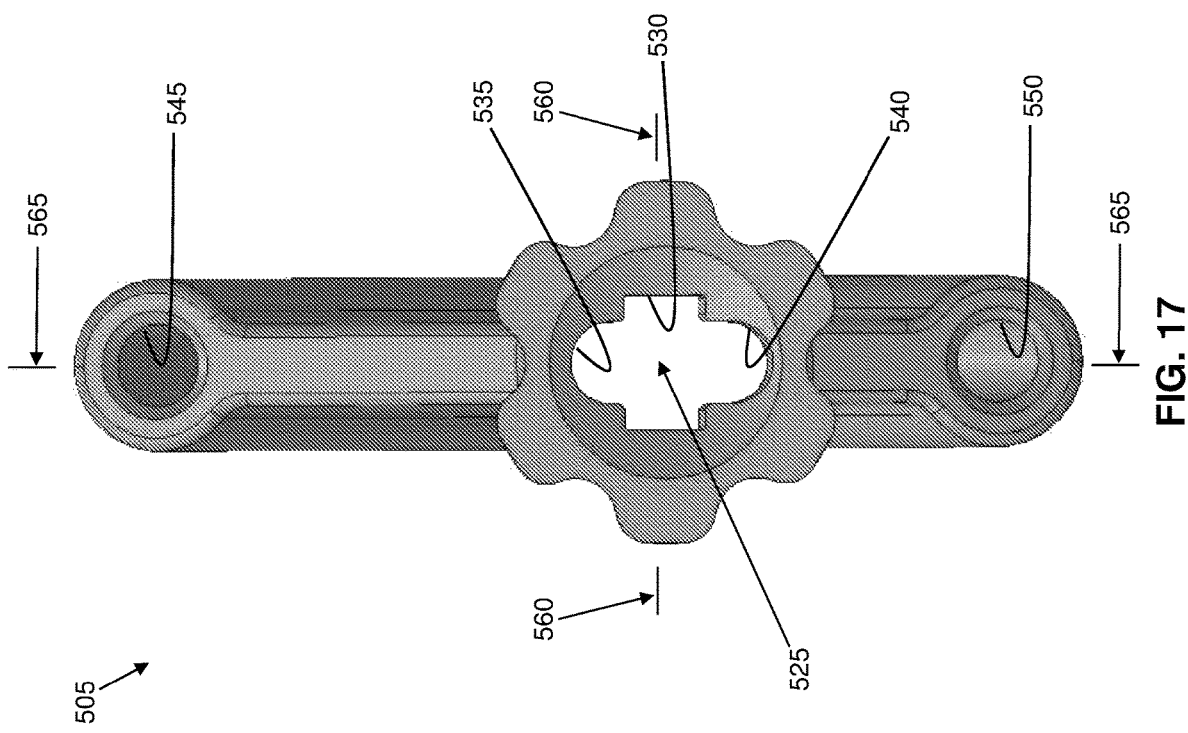

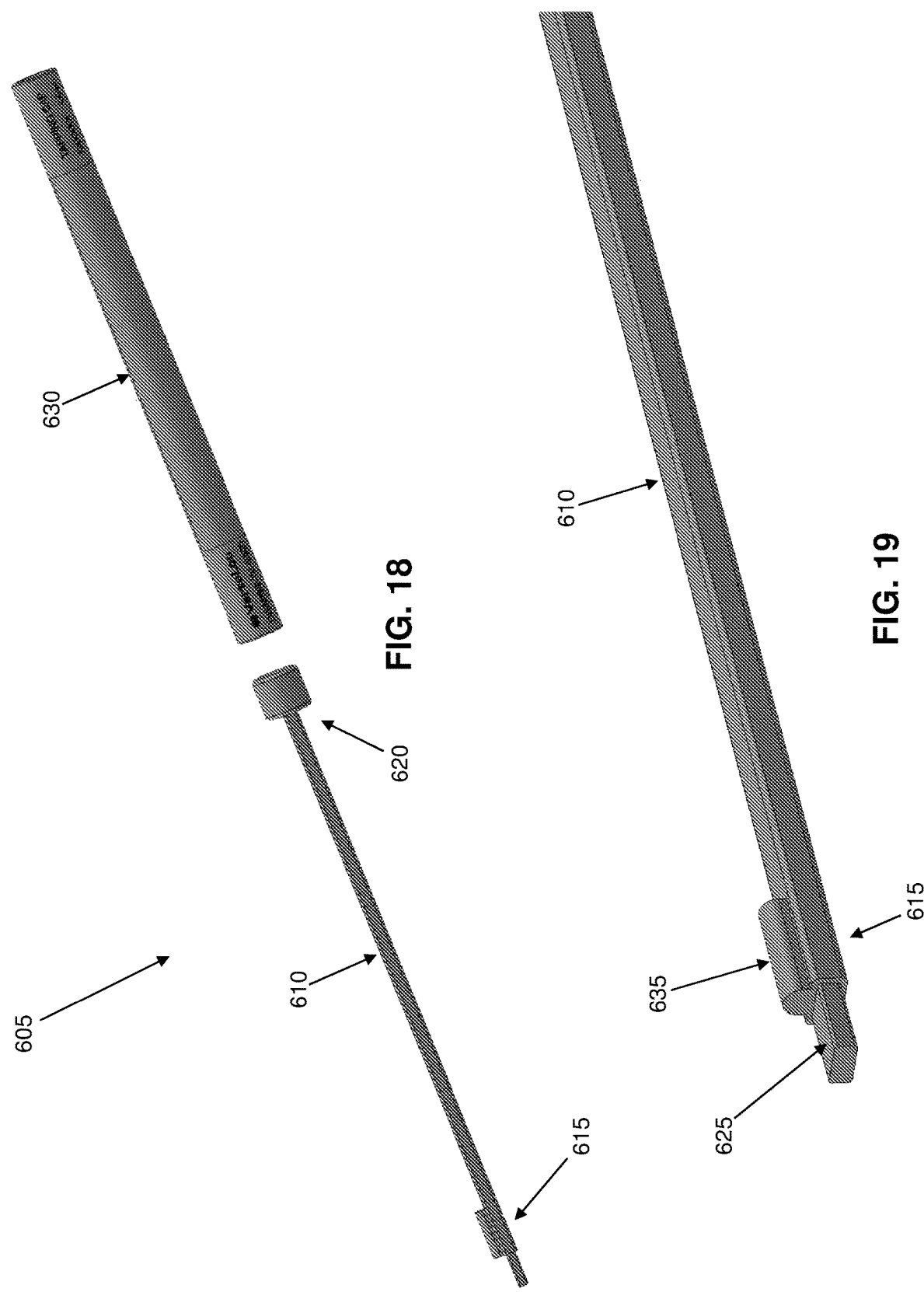

STEP 1: PLACE JOINT LOCATOR INTO THE CERVICAL FACET JOINT

STEP 1: PLACE JOINT LOCATOR INTO THE CERVICAL FACET JOINT

STEP 2: SLIDE JOINT DECORTICATOR OVER JOINT LOCATOR AND TWIST TO DECORTICATE FACETS (OPTIONAL)

STEP 2: SLIDE JOINT DECORTICATOR OVER JOINT LOCATOR AND TWIST TO DECORTICATE FACETS (OPTIONAL)

STEP 2: SLIDE JOINT DECORTICATOR OVER JOINT LOCATOR AND TWIST TO DECORTICATE FACETS (OPTIONAL)

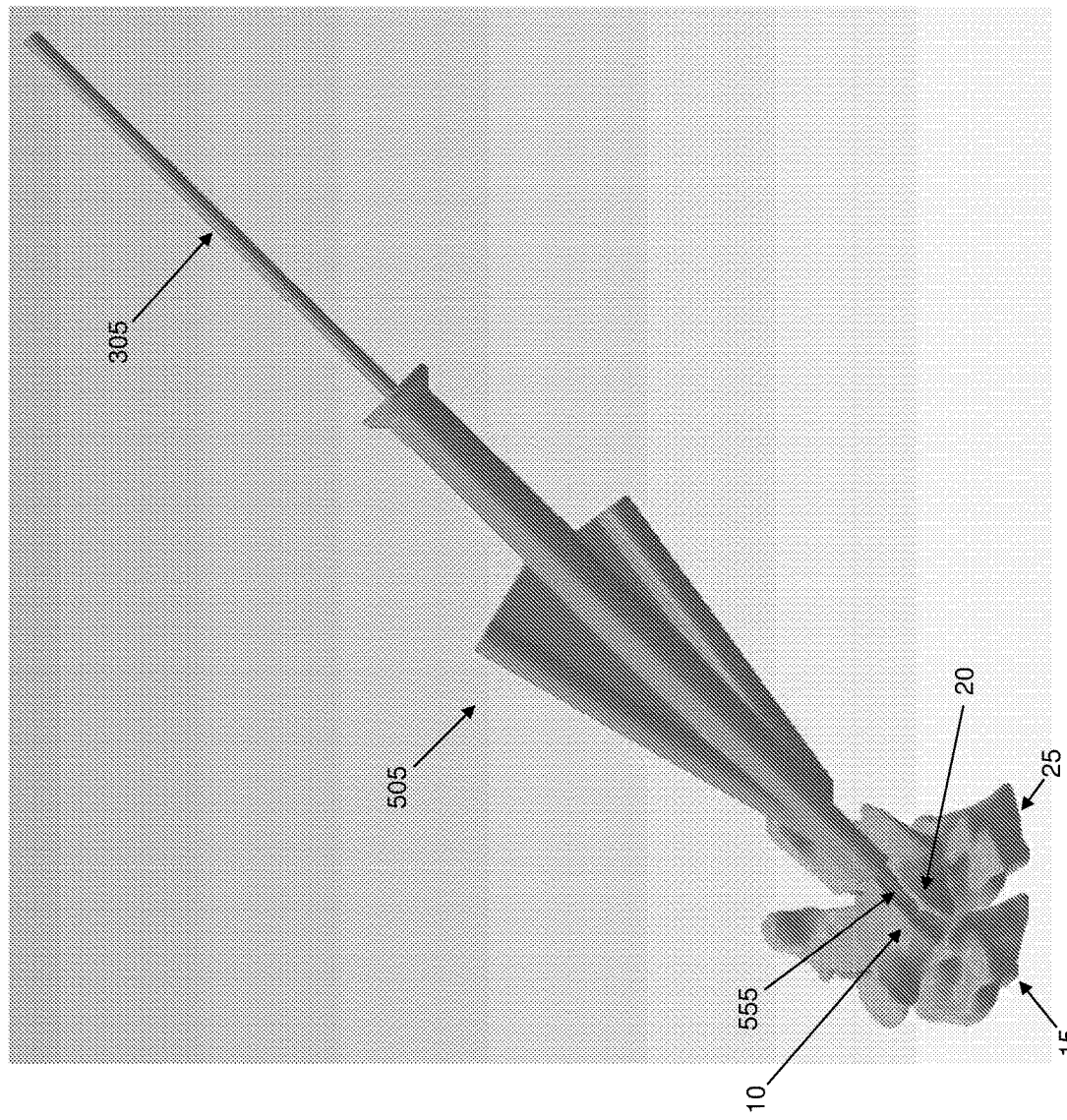

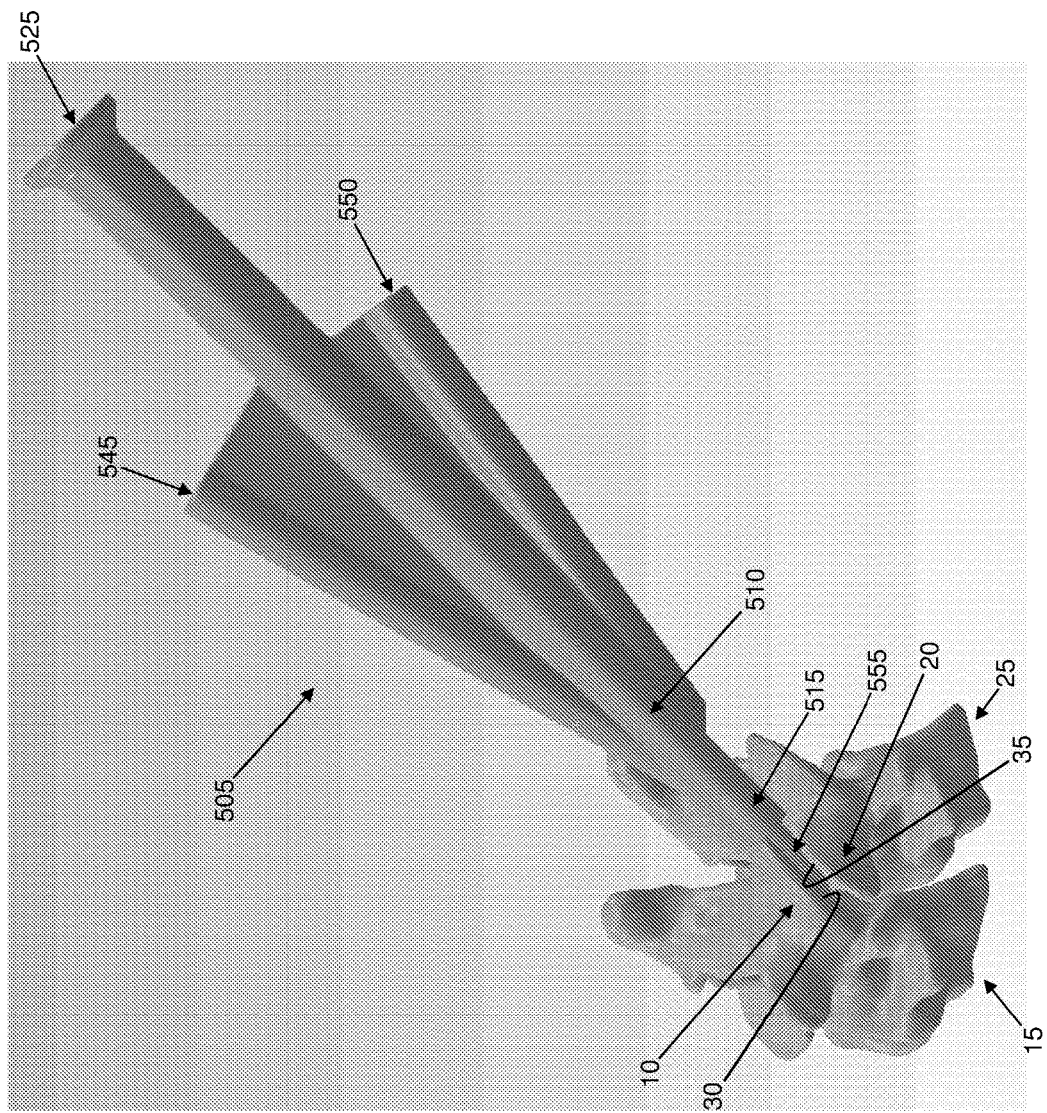
FIG. 25 STEP 4: REMOVE (PULL OUT) JOINT LOCATOR

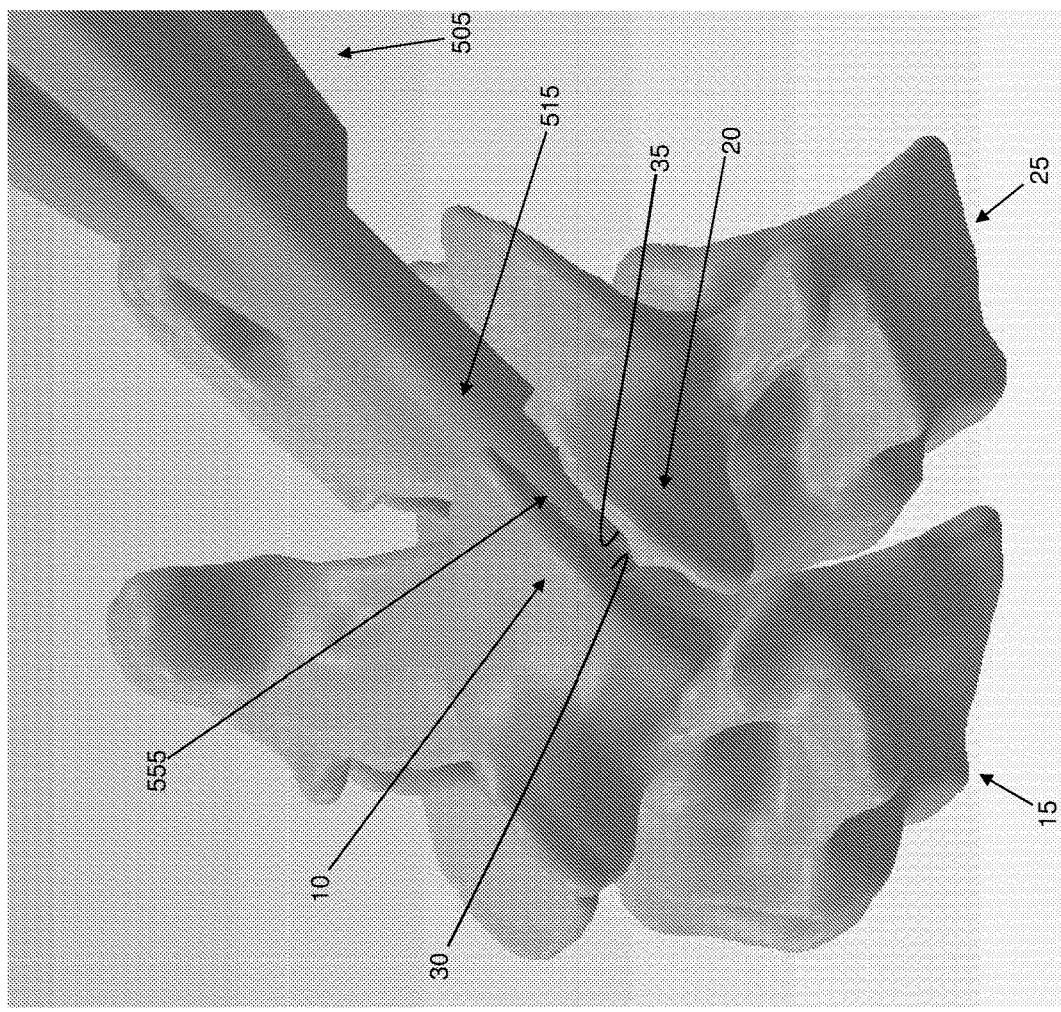

STEP 4: REMOVE (PULL OUT) JOINT LOCATOR

STEP 6: DRILL OPPOSITE FACET TO CREATE POCKET

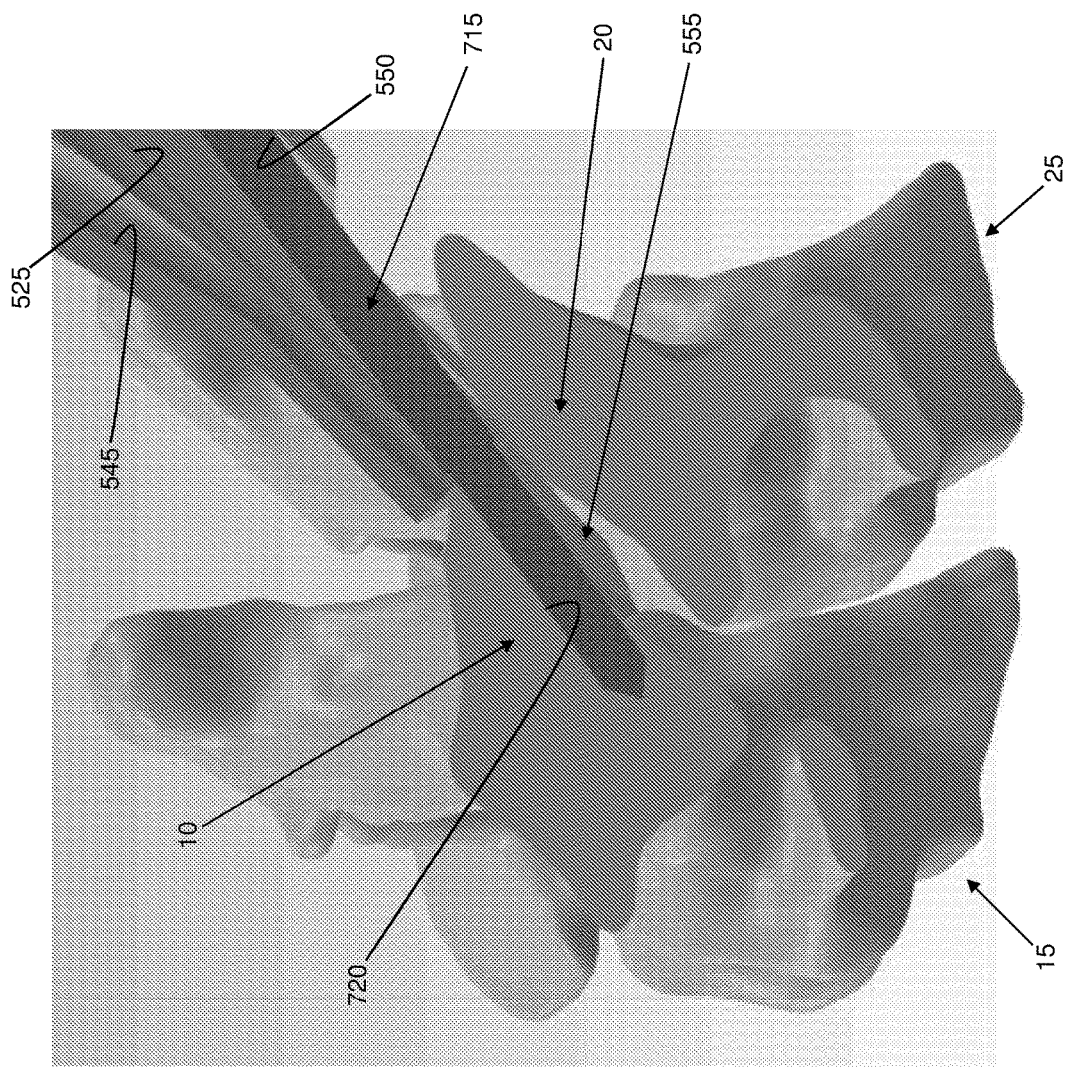

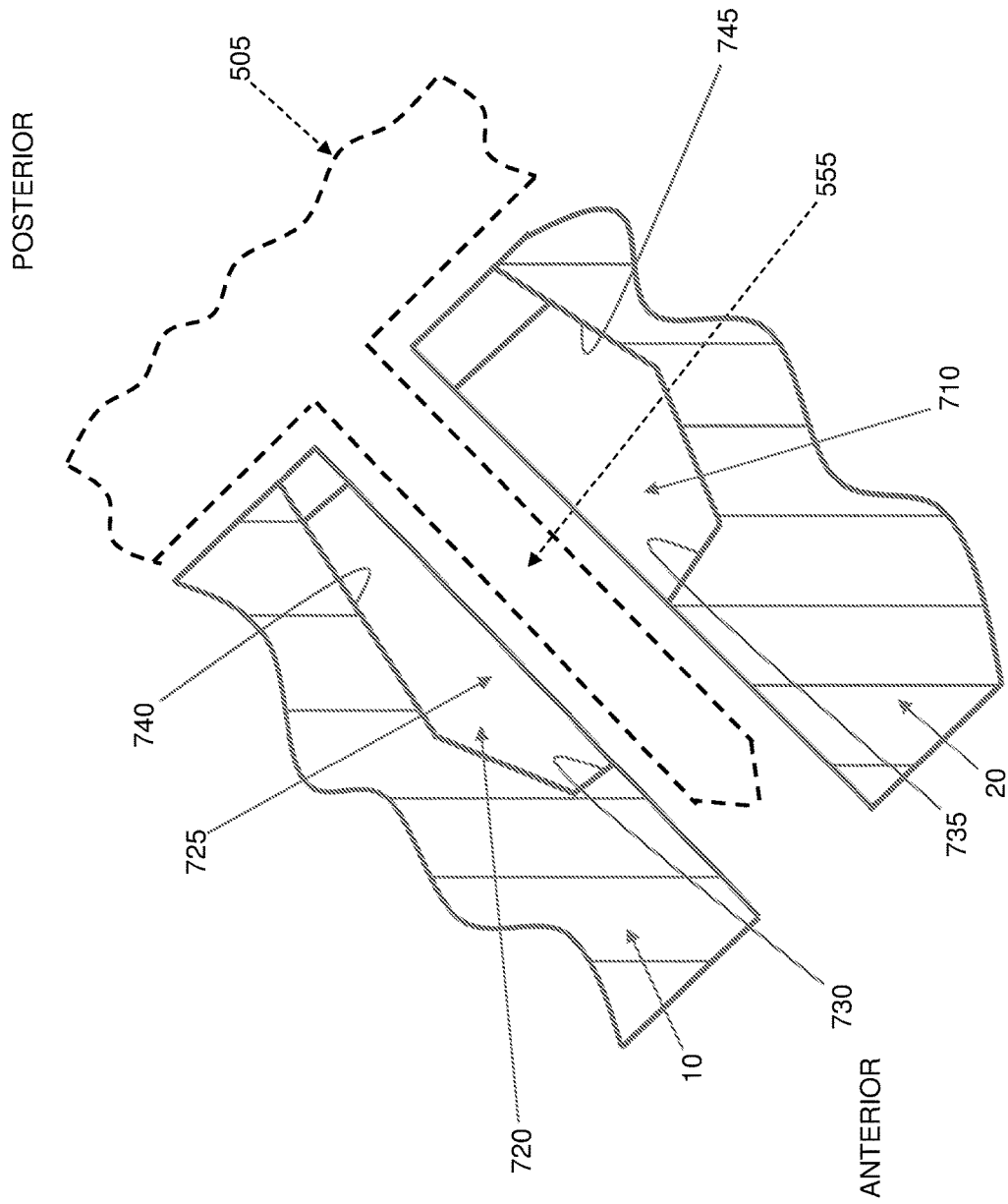
FIG. 31 STEP 6: DRILL OPPOSITE FACET TO CREATE POCKET

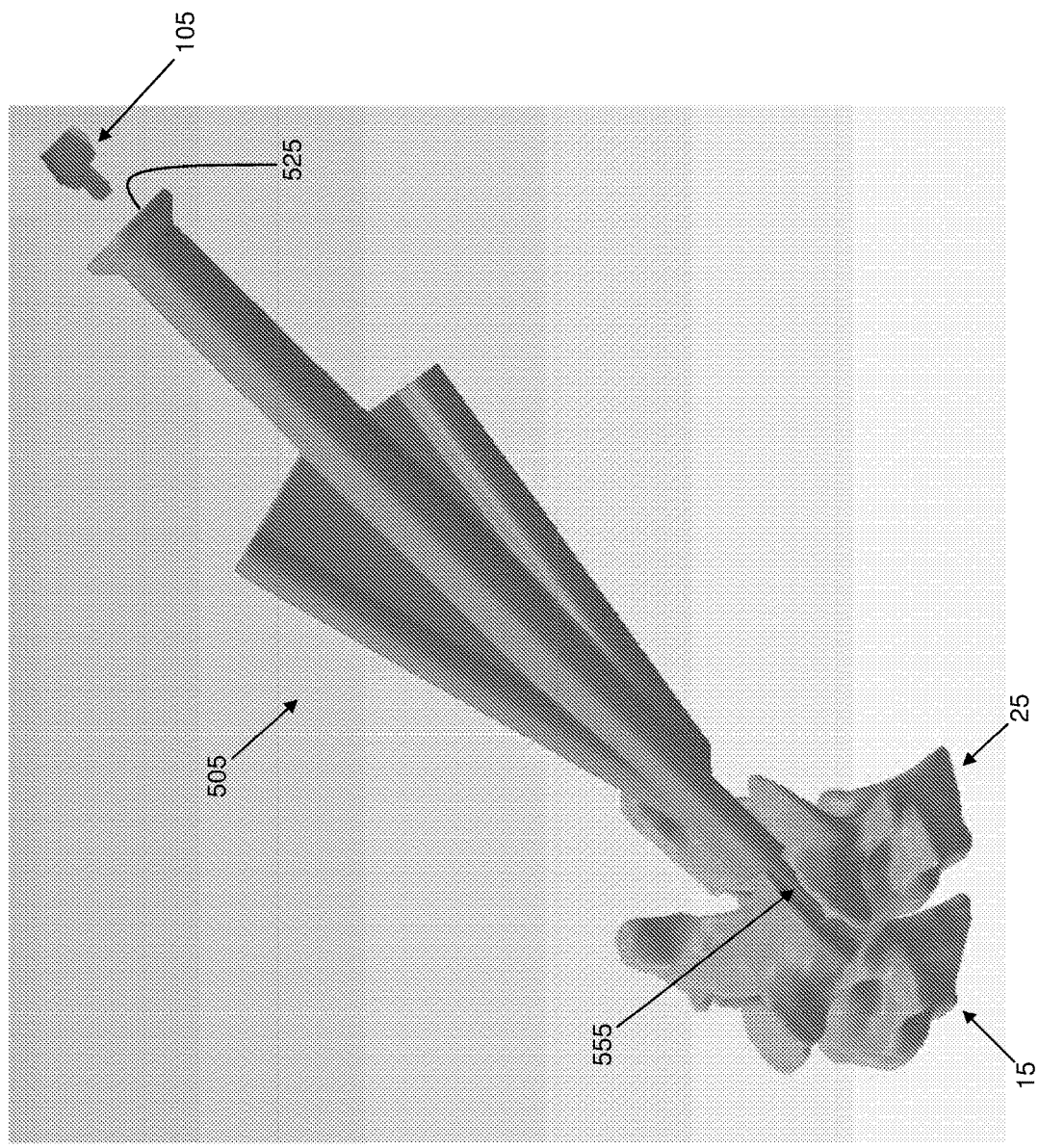
FIG. 32 STEP 7: PLACE IMPLANT INTO CANNULA

STEP 7: PLACE IMPLANT INTO CANNULA

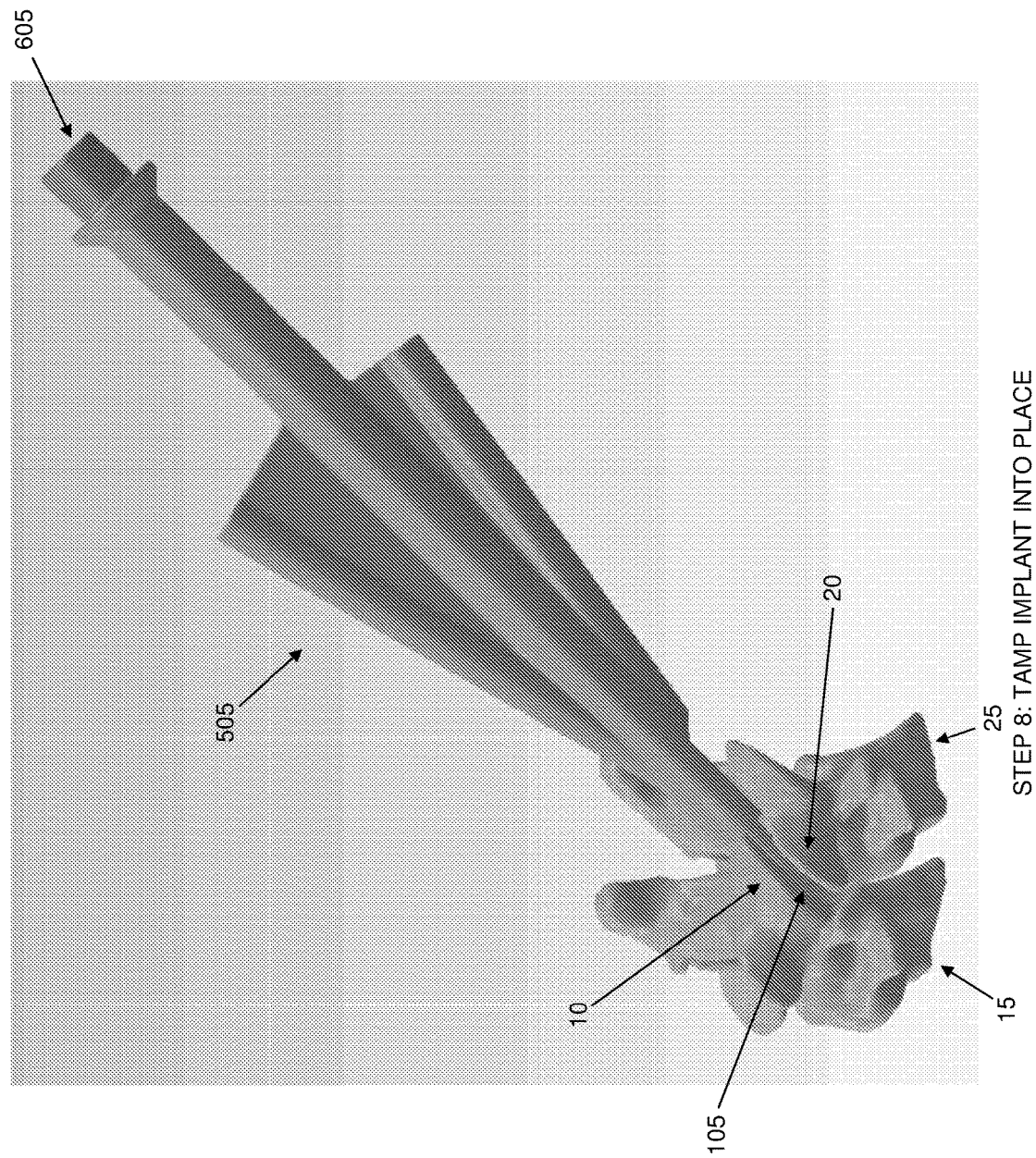

STEP 8: TAMP IMPLANT INTO PLACE

METHOD AND APPARATUS FOR SPINAL FACET FUSION

REFERENCE TO PENDING PRIOR PATENT APPLICATIONS

This patent application is a continuation of pending prior U.S. patent application Ser. No. 16/879,385, filed May 20, 2020 by VGI Medical, LLC and Tov Vestgaarden et al. for METHOD AND APPARATUS FOR SPINAL FACET FUSION, which patent application is a continuation of prior U.S. patent application Ser. No. 15/631,670, filed Jun. 23, 2017 by VGI Medical, LLC for METHOD AND APPARATUS FOR SPINAL FACET FUSION, which patent application claims benefit of prior U.S. Provisional Patent Application Ser. No. 62/353,809, filed Jun. 23, 2016 by VGI Medical, LLC and Tov Vestgaarden et al. for METHOD AND APPARATUS FOR SPINAL FACET FUSION.

The three (3) above-identified patent applications are hereby incorporated herein by reference.

FIELD OF THE INVENTION

This invention relates to surgical methods and apparatus in general, and more particularly to surgical methods and apparatus for fusing spinal facets.

BACKGROUND OF THE INVENTION

Disc herniation is a condition where a spinal disc bulges from between two vertebral bodies and impinges on adjacent nerves, thereby causing pain. The current standard of care for surgically treating disc herniation in patients who have chronic pain and who have (or are likely to develop) associated spinal instability is spinal fixation. Spinal fixation procedures are intended to relieve the impingement on the nerves by removing the portion of the disc and/or bone responsible for compressing the neural structures and destabilizing the spine. The excised disc or bone is replaced with one or more intervertebral implants, or spacers, placed between the adjacent vertebral bodies.

In some cases, the spinal fixation leaves the affected spinal segment unstable. In this case, the spinal facets (i.e., the bony fins extending upwardly and downwardly from the rear of each vertebral body) can misengage with one another. The misengagement of the spinal facets can result in substantial pain to the patient. Furthermore, when left untreated, such misengagement of the spinal facets can result in the degeneration of the cartilage located between opposing facet surfaces, ultimately resulting in osteoarthritis, which can in turn lead to worsening pain for the patient.

Thus, where the patient suffers from spinal instability, it can be helpful to stabilize the facet joints as well as the vertebral bodies. The facet joints are frequently stabilized by fusing the spinal facets in position relative to one another.

In addition to providing stability, fusing the spinal facets can also be beneficial in other situations as well. By way of example but not limitation, osteoarthritis (a condition involving the degeneration, or wearing away, of the cartilage at the end of bones) frequently occurs in the facet joints. The prescribed treatment for osteoarthritis disorders depends on the location, severity and duration of the disorder. In some cases, non-operative procedures (including bed rest, medication, lifestyle modifications, exercise, physical therapy, chiropractic care and steroid injections) may be satisfactory treatment. However, in other cases, surgical intervention may be necessary. In cases where surgical intervention is prescribed, spinal facet fusion may be desirable.

A minimally-invasive, percutaneous approach for fusing spinal facets was proposed by Stein et al. ("Stein") in 1993. The Stein approach involved using a conical plug, made from cortical bone and disposed in a hole formed intermediate the spinal facet joint, to facilitate the fusing of opposing facet surfaces. However, the clinical success of this approach was limited. This is believed to be because the Stein approach did not adequately restrict facet motion. In particular, it is believed that movement of Stein's conical plug within its hole permitted unwanted facet movement to occur, thereby undermining facet fusion. Furthermore, the Stein approach also suffered from plug failure and plug migration.

Thus there is a need for a new and improved approach for effecting spinal facet fusion.

In addition to the foregoing, it should be appreciated that the spine comprises various regions having differing characteristics. More particularly, the first seven vertebrae (C1-C7) are the so-called cervical vertebrae, the next twelve vertebrae (T1-T12) are the so-called thoracic vertebrae, and the next five vertebrae (L1-L5) are the so-called lumbar vertebrae. Beneath the lumbar vertebrae are the five fused vertebrae of the sacrum, and then the four fused vertebrae of the coccyx (or tailbone). The facet joints in the cervical vertebrae can differ somewhat from the facet joints in the thoracic vertebrae and lumbar vertebrae, e.g., the facet joints in the cervical vertebrae are typically oriented generally horizontal to the longitudinal axis of the spine, whereas the facet joints of the thoracic vertebrae and the facet joints of the lumbar vertebrae are typically oriented generally vertical to the longitudinal axis of the spine. It has been found that it can be significantly more difficult to successfully effect spinal facet fusion in the cervical vertebrae than in the thoracic vertebrae and in the lumbar vertebrae.

Thus there is a need for a new and improved approach for effecting spinal facet fusion in the cervical vertebrae.

SUMMARY OF THE INVENTION

The present invention provides a novel method and apparatus for effecting spinal facet fusion, and is particularly advantageous for use in effecting spinal facet fusion in the cervical vertebrae. More particularly, the present invention comprises the provision and use of a novel spinal facet fusion implant (sometimes hereinafter referred to as a "novel fusion implant") for disposition between the opposing articular surfaces of a facet joint, including the facet joint of a cervical vertebrae, whereby to immobilize the facet joint and facilitate fusion between the opposing facets. The present invention also comprises the provision and use of novel instrumentation for installing the novel spinal facet fusion implant in a facet joint.

In one preferred form of the invention, there is provided a spinal facet fusion implant comprising:

an elongated body having a distal end, a proximal end and a longitudinal axis extending between the distal end and the proximal end, the elongated body being characterized by a superior body surface and an inferior body surface;

a superior stabilizer extending outwardly from the superior body surface, the superior stabilizer being characterized by a superior stabilizer surface; and an inferior stabilizer extending outwardly from the inferior body surface, the inferior stabilizer being characterized by an inferior stabilizer surface;

wherein (i) the superior body surface and the inferior body surface are tapered relative to one another, and/or (ii) the superior stabilizer surface and the inferior stabilizer surface are tapered relative to one another.

In another preferred form of the invention, there is provided a system for effecting spinal facet fusion, the system comprising:
  a spinal facet fusion implant comprising:
    an elongated body having a distal end, a proximal end and a longitudinal axis extending between the distal end and the proximal end, the elongated body being characterized by a superior body surface and an inferior body surface;
    a superior stabilizer extending outwardly from the superior body surface, the superior stabilizer being characterized by a superior stabilizer surface; and
    an inferior stabilizer extending outwardly from the inferior body surface, the inferior stabilizer being characterized by an inferior stabilizer surface;
    wherein (i) the superior body surface and the inferior body surface are tapered relative to one another, and/or (ii) the superior stabilizer surface and the inferior stabilizer surface are tapered relative to one another;
  a drill guide/cannula for preparing the anatomy to receive the spinal facet fusion implant and for delivering the spinal facet fusion implant to the anatomy, the drill guide/cannula comprising:
    a body having a distal end, a proximal end and a longitudinal axis extending therebetween, the distal end of the body being configured for engaging the gap between a descending facet of a first vertebra and an ascending facet of a second vertebra;
    a central lumen extending between the distal end of the body and the proximal end of the body, the central lumen having a cross-sectional profile which matches the cross-sectional profile of the spinal facet fusion implant such that the spinal facet fusion implant can be introduced into the proximal end of the central lumen, advanced distally along the central lumen, and advanced distally out of the distal end of the central lumen and into the gap between the descending facet of the first vertebra and the ascending facet of the second vertebra;
    a first drill guide angled relative to the longitudinal axis of the central lumen, the first drill guide being configured to receive a drill therein so as to drill a first seat in the descending facet of the first vertebra;
    a second drill guide angled relative to the longitudinal axis of the central lumen, the second drill guide being configured to receive a drill therein so as to drill a second seat in the ascending facet of the second vertebra;
    wherein the first seat in the descending facet of the first vertebra is sized and angled so as to receive the superior stabilizer of the spinal facet fusion implant when the spinal facet fusion implant is advanced into the gap between the first vertebra and the second vertebra; and
    wherein the second seat in the ascending facet of the second vertebra is sized and angled so as to receive the inferior stabilizer of the spinal facet fusion implant when the spinal facet fusion implant is advanced into the gap between the first vertebra and the second vertebra.

In another preferred form of the invention, there is provided a system for effecting spinal facet fusion, the system comprising:
  a spinal facet fusion implant, the spinal facet fusion implant comprising a taper; and
  a drill guide/cannula for preparing the anatomy to receive the spinal facet fusion implant and for delivering the spinal facet fusion implant to the anatomy, the drill guide/cannula comprising:
    a body having a distal end, a proximal end and a longitudinal axis extending therebetween, the distal end of the body being configured for engaging the gap between a descending facet of a first vertebra and an ascending facet of a second vertebra;
    a central lumen extending between the distal end of the body and the proximal end of the body, the central lumen having a cross-sectional profile which matches the cross-sectional profile of the spinal facet fusion implant such that the spinal facet fusion implant can be introduced into the proximal end of the central lumen, advanced distally along the central lumen, and advanced distally out of the distal end of the central lumen and into the gap between the descending facet of the first vertebra and the ascending facet of the second vertebra;
    a first drill guide angled relative to the longitudinal axis of the central lumen, the first drill guide being configured to receive a drill therein so as to drill a first seat in the descending facet of the first vertebra;
    a second drill guide angled relative to the longitudinal axis of the central lumen, the second drill guide being configured to receive a drill therein so as to drill a second seat in the ascending facet of the second vertebra;
    wherein the first seat in the descending facet of the first vertebra and the second seat in the ascending facet of the second vertebra are sized and angled so as to receive the spinal facet fusion implant therein when the spinal facet fusion implant is advanced into the gap between the first vertebra and the second vertebra.

In another preferred form of the invention, there is provided a method for effecting spinal facet fusion, the method comprising:
  providing a spinal facet fusion implant comprising:
    an elongated body having a distal end, a proximal end and a longitudinal axis extending between the distal end and the proximal end, the elongated body being characterized by a superior body surface and an inferior body surface;
    a superior stabilizer extending outwardly from the superior body surface, the superior stabilizer being characterized by a superior stabilizer surface; and
    an inferior stabilizer extending outwardly from the inferior body surface, the inferior stabilizer being characterized by an inferior stabilizer surface;
    wherein (i) the superior body surface and the inferior body surface are tapered relative to one another, and/or (ii) the superior stabilizer surface and the inferior stabilizer surface are tapered relative to one another;
  providing a drill guide/cannula for preparing the anatomy to receive the spinal facet fusion implant and for delivering the spinal facet fusion implant to the anatomy, the drill guide/cannula comprising:
    a body having a distal end, a proximal end and a longitudinal axis extending therebetween, the distal end of the body being configured for engaging the gap between a descending facet of a first vertebra and an ascending facet of a second vertebra;

a central lumen extending between the distal end of the body and the proximal end of the body, the central lumen having a cross-sectional profile which matches the cross-sectional profile of the spinal facet fusion implant such that the spinal facet fusion implant can be introduced into the proximal end of the central lumen, advanced distally along the central lumen, and advanced distally out of the distal end of the central lumen and into the gap between the descending facet of the first vertebra and the ascending facet of the second vertebra;

a first drill guide angled relative to the longitudinal axis of the central lumen, the first drill guide being configured to receive a drill therein;

a second drill guide angled relative to the longitudinal axis of the central lumen, the second drill guide being configured to receive a drill therein;

advancing a drill into the first drill guide so as to form a first seat in the descending facet of the first vertebra;

advancing a drill into the second drill guide so as to form a second seat in the ascending facet of the second vertebra;

advancing the spinal facet fusion implant into the gap between the first vertebra and the second vertebra so that (i) the superior stabilizer is disposed in the first seat of the descending facet of the first vertebra, and (ii) the inferior stabilizer is disposed in the second seat of the ascending facet of the second vertebra.

In another preferred form of the invention, there is provided a method for effecting spinal facet fusion, the method comprising:

providing a spinal facet fusion implant, the spinal facet fusion implant comprising a taper;

forming a first seat in the descending facet of a first vertebra, and forming a second seat in the ascending facet of a second vertebra, wherein at least one of the first seat and the second seat comprises a taper; and advancing the spinal facet fusion implant into the gap between the first vertebra and the second vertebra so that the spinal facet fusion implant is disposed in the first seat of the descending facet and the second seat of the ascending facet of the second vertebra.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 4 is a schematic view showing a facet joint between the C3 cervical vertebra and the C4 cervical vertebra;

FIGS. 5-10 are schematic views showing a novel fusion implant formed in accordance with the present invention;

FIGS. 15-17 are schematic views showing a drill guide/cannula which may be used to prepare bone to receive the novel fusion implant of FIGS. 5-10 and which may be used to deploy the novel fusion implant of FIGS. 5-10;

FIGS. 18 and 19 are schematic views showing a tamp which may be used to deploy the novel fusion implant of FIGS. 5-10;

FIGS. 20, 21, 21A, 22, 23, 23A, 24-26, 26A, 27-32, 32A, 33-36 are schematic views showing the novel fusion implant of FIGS. 5-10 being installed in a facet joint;

DETAILED DESCRIPTION OF THE PREFERRED EMBODIMENTS

The Cervical Vertebrae in General

Figure 1:
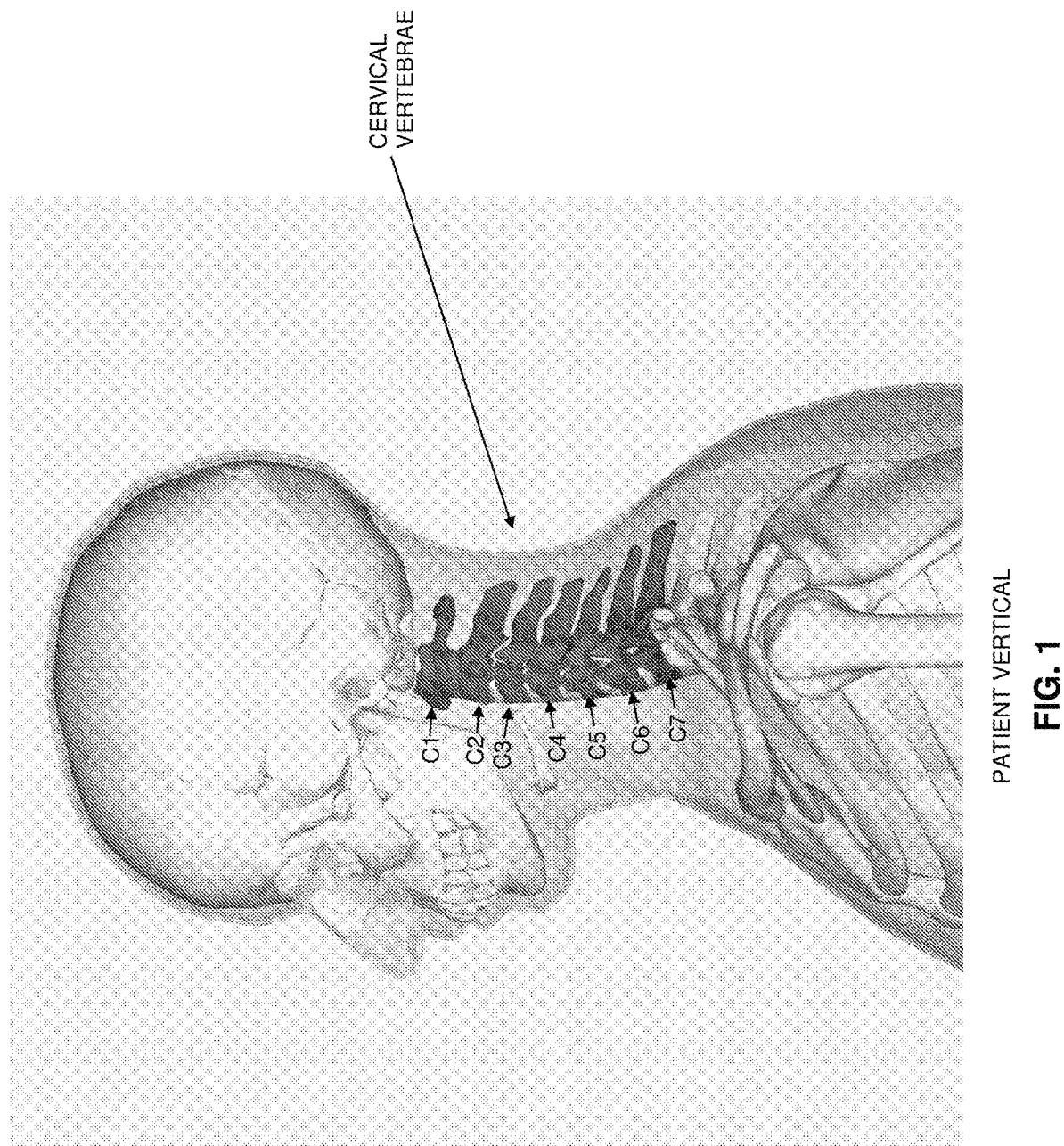
FIGS. 1-3 are schematic views showing the seven cervical vertebrae (C1-C7)
Figure 2:
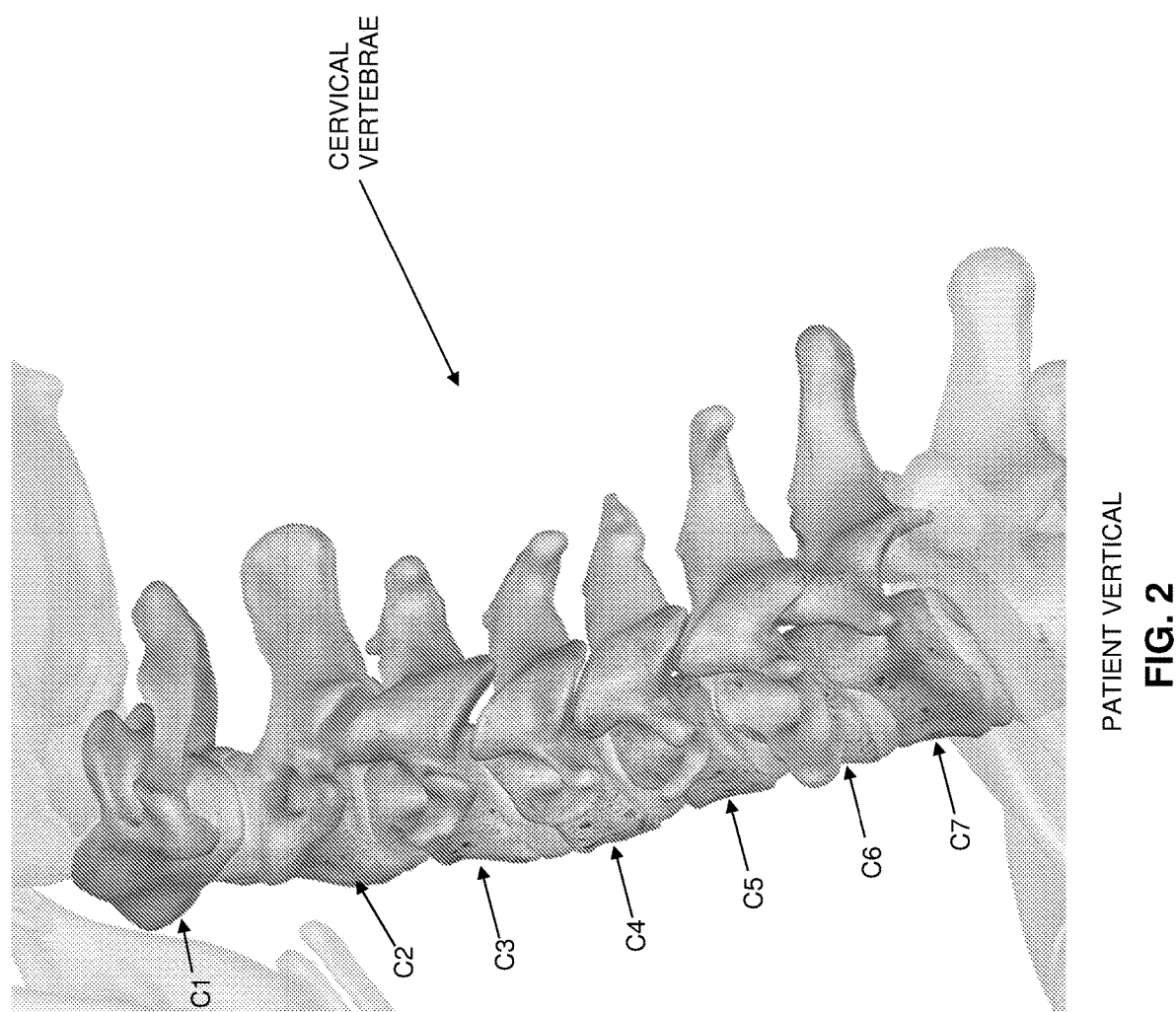
Figure 3:
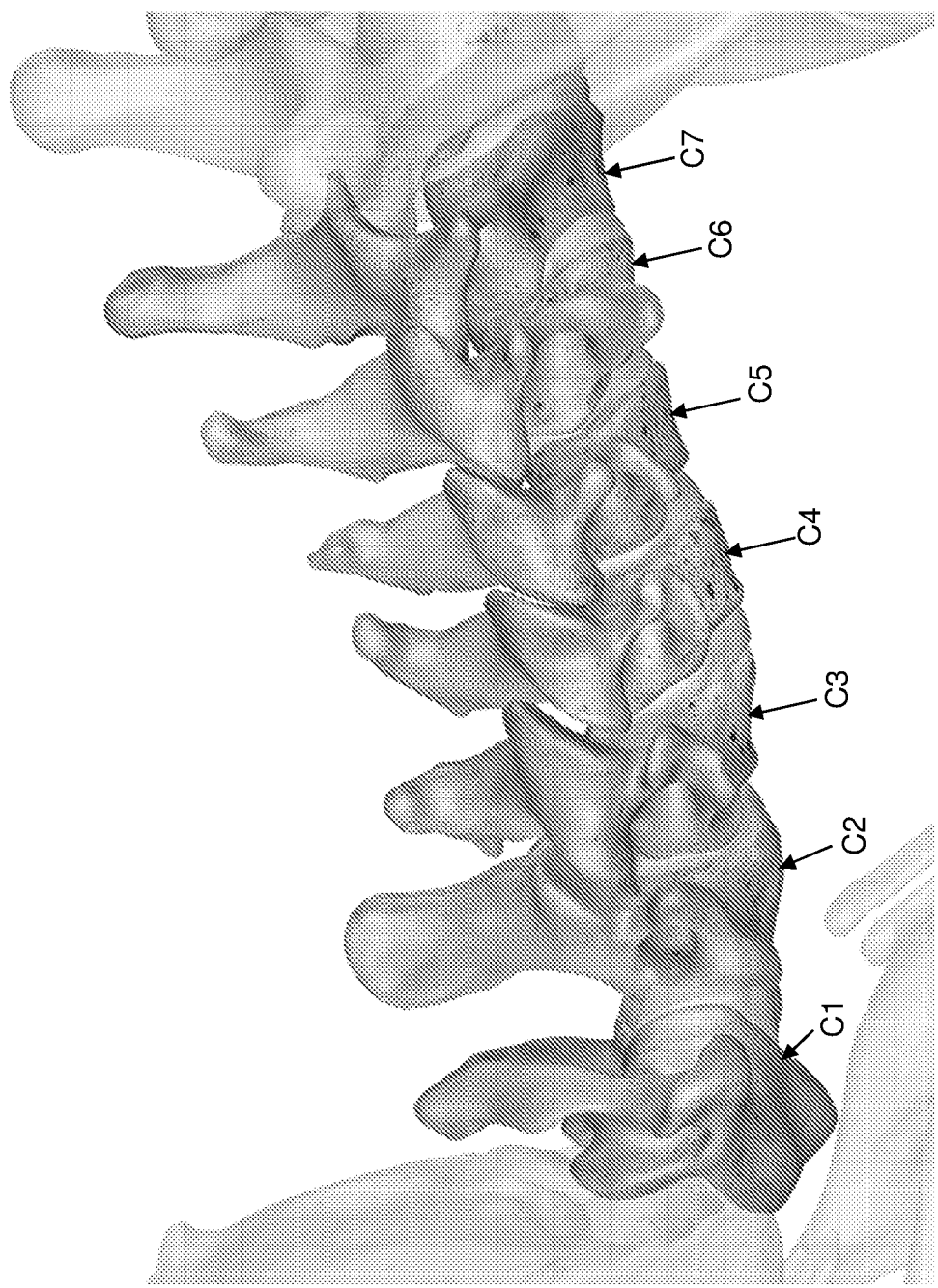

Looking first at FIGS. 1-3, there is shown the seven cervical vertebrae (C1-C7) which are located at the top of the spine. FIGS. 1 and 2 show the seven cervical vertebrae being oriented vertically (e.g., such as when the patient is sitting or standing), and FIG. 3 shows the seven cervical vertebrae being oriented horizontally (e.g., such as when the patient is lying down). FIG. 4 shows an exemplary facet joint 5 located between a descending facet 10 of a C3 cervical vertebra 15 and an ascending facet 20 of a C4 cervical vertebra 25. In facet joint 5, face 30 of descending facet 10 of C3 cervical vertebra 15 engages face 35 of ascending facet 20 of C4 cervical vertebra 25.

The Novel Fusion Implant

Looking next at FIGS. 5-10, there is shown a novel spinal facet fusion implant 105 formed in accordance with the present invention. Fusion implant 105 generally comprises a body 110, a superior stabilizer 115 and an inferior stabilizer 120. As used herein, the term "superior stabilizer" is intended to identify the stabilizer which engages the descending facet of a facet joint (e.g., descending facet 10 of C3 cervical vertebra 15), and the term "inferior stabilizer" is intended to identify the stabilizer which engages the ascending facet of a facet joint (e.g., ascending facet 20 of a C4 cervical vertebra 25).

Body 110 comprises an elongated element having structural integrity. More particularly, body 110 generally comprises a distal end surface 125, a proximal end surface 130, a superior surface 135 extending distally from proximal end surface 130, and an inferior surface 140 extending distally from proximal end surface 130. Superior surface 135 and inferior surface 140 diverge as they extend distally from proximal end surface 130, i.e., so that the "height" of the distal end of body 110 is greater than the "height" of the proximal end of body 110. A superior beveled surface 145 connects the distal end of superior surface 135 with distal end surface 125, and an inferior beveled surface 150 connects the distal end of inferior surface 140 with distal end surface 125. Body 110 further comprises a medial side surface 155 and a lateral side surface 160, each of which is bounded by the aforementioned distal end surface 125, proximal end surface 130, superior surface 135, inferior surface 140, superior beveled surface 145, and inferior beveled surface 150.

In one preferred form of the invention, the "height" of proximal end surface 130 is sized to be approximately the width of the gap between the two facets of a facet joint.

Superior stabilizer 115 generally comprises a distal end surface 165, a proximal end surface 170, a rounded superior surface 175 extending distally from proximal end surface 170, and a superior beveled surface 180 which connects distal end surface 165 with generally rounded superior surface 175. Superior stabilizer 115 further comprises a medial side surface 185 and a lateral side surface 190, each of which is bounded by the aforementioned distal end surface 165, proximal end surface 170, rounded superior surface 175 and superior beveled surface 180.

Inferior stabilizer 120 generally comprises a distal end surface 195, a proximal end surface 200, a rounded inferior surface 205 extending distally from proximal end surface 200, and an inferior beveled surface 210 which connects distal end surface 195 with generally rounded inferior surface 205. Inferior stabilizer 120 further comprises a medial side surface 215 and a lateral side surface 220, each of which is bounded by the aforementioned distal end surface 195, proximal end surface 200, rounded inferior surface 205 and inferior beveled surface 210.

In one preferred form of the invention, and as seen in FIGS. 5-10, proximal end surfaces 130, 170 and 200 are substantially co-planar.

In one preferred form of the invention, the tangent line 225 (FIG. 6) of rounded superior surface 175 of superior stabilizer 115 extends at an angle $\alpha$ (e.g., of approximately 10 degrees) relative to the longitudinal axis 230 of body 110, and the tangent line 235 of rounded inferior surface 205 of inferior stabilizer 120 extends at an angle $\beta$ (of approximately 15 degrees) relative to the longitudinal axis 230 of body 110.

In one preferred form of the invention, distal end surface 165 of superior stabilizer 115 is disposed distal to distal end surface 195 of inferior stabilizer 120.

Thus it will be seen that, in one preferred form of the invention, superior stabilizer 115 and inferior stabilizer 120 have different configurations.

As will hereinafter be discussed in further detail, body 110 of novel fusion implant 105 is intended to be disposed in the space between the descending facet of a facet joint and the opposing ascending facet of a facet joint (e.g., in the space between face 30 of descending facet 10 of C3 cervical vertebra 15 and face 35 of ascending facet 20 of C4 cervical vertebra 25); superior stabilizer 115 is intended to be disposed in a seat formed in the descending facet of the facet joint (e.g., a seat formed in descending facet 10 of C3 cervical vertebra 15); and inferior stabilizer 120 is intended to be disposed in a seat formed in the ascending facet of the facet joint (e.g., a seat formed in ascending facet 20 of C4 cervical vertebra 25), whereby to immobilize the facet joint and facilitate fusing of the facet joint. In this respect it should be appreciated that, and as will hereinafter be discussed, fusion implant 105 preferably makes a "friction fit" with the two facets of the facet joint, and superior stabilizer 115 and inferior stabilizer 120 are seated in descending facet 10 and ascending facet 20, respectively, so as to lock the facets against movement relative to one another. Significantly, the tapered configuration of novel fusion implant 105, when seated in an appropriately-configured pocket formed in the descending facet 10 and ascending facet 20 of a facet joint, locks the fusion implant against anterior or posterior movement. The tapered configuration of novel fusion implant 105 also helps create/restore lordosis.

It should be appreciated that novel fusion implant 105 is particularly well suited for use in fusing a cervical facet joint.

And as will hereinafter be discussed in further detail, novel fusion implant 105 is intended to be inserted into a facet joint using a posterior approach. Such a posterior approach is familiar to spine surgeons (thereby providing an increased level of comfort for the surgeon), and also minimizes the possibility of damage to the spinal cord during fusion implant insertion.

Preferred Instrumentation for Installing the Novel Fusion Implant

Figure 11:
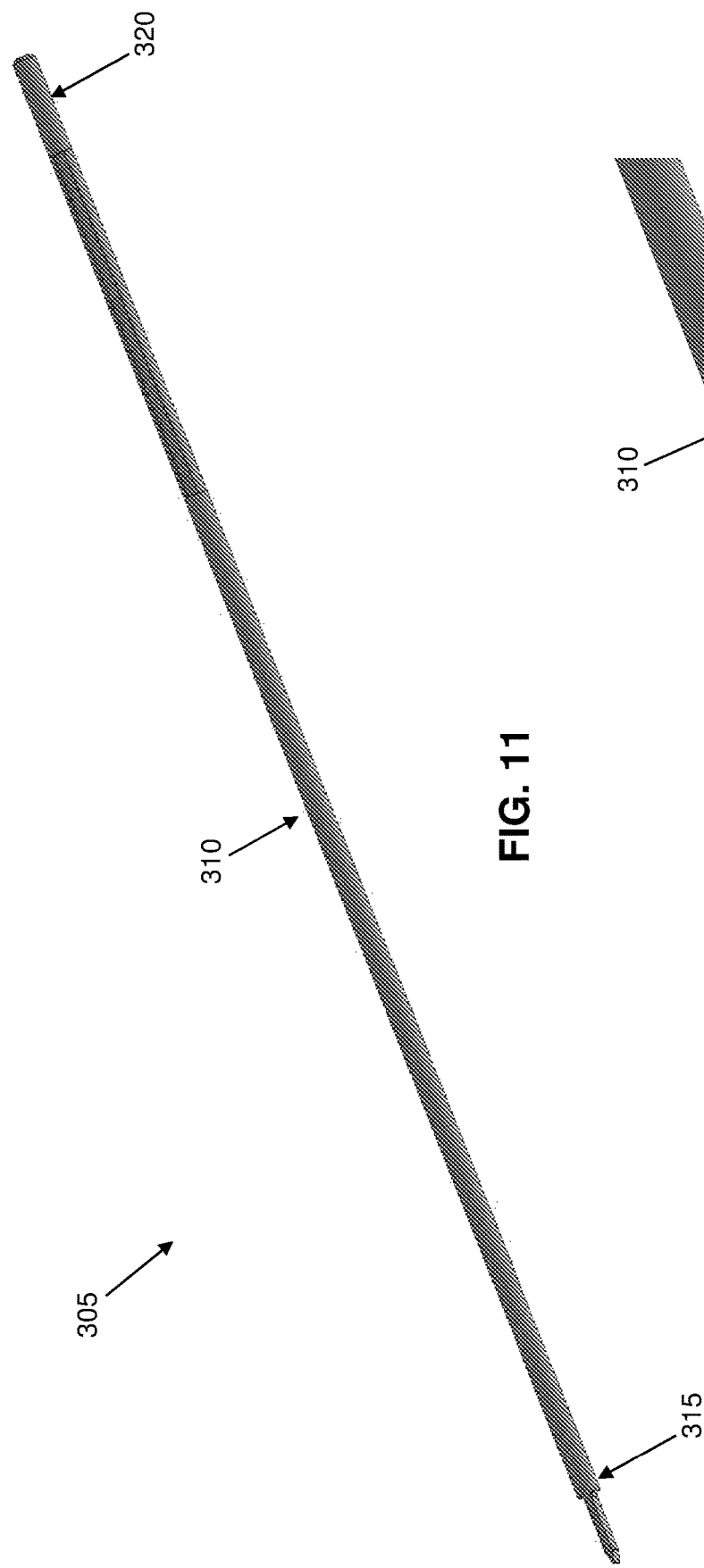
FIGS. 11 and 12 are schematic views showing a joint locator which may be used to deploy the novel fusion implant of FIGS. 5-10.
Figure 12:
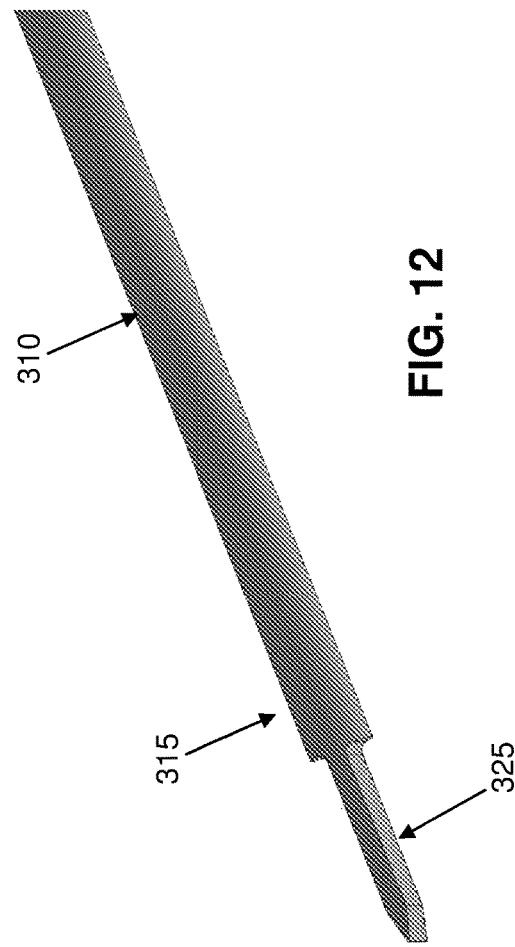
Figure 13:
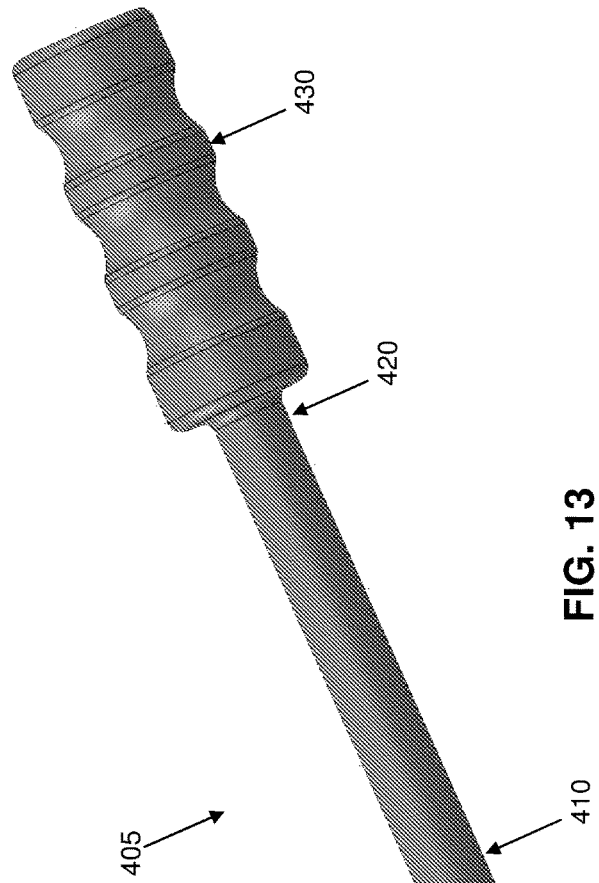
FIGS. 13 and 14 are schematic views showing a joint decorticator which may be used to decorticate bone to promote fusion.
Figure 14:
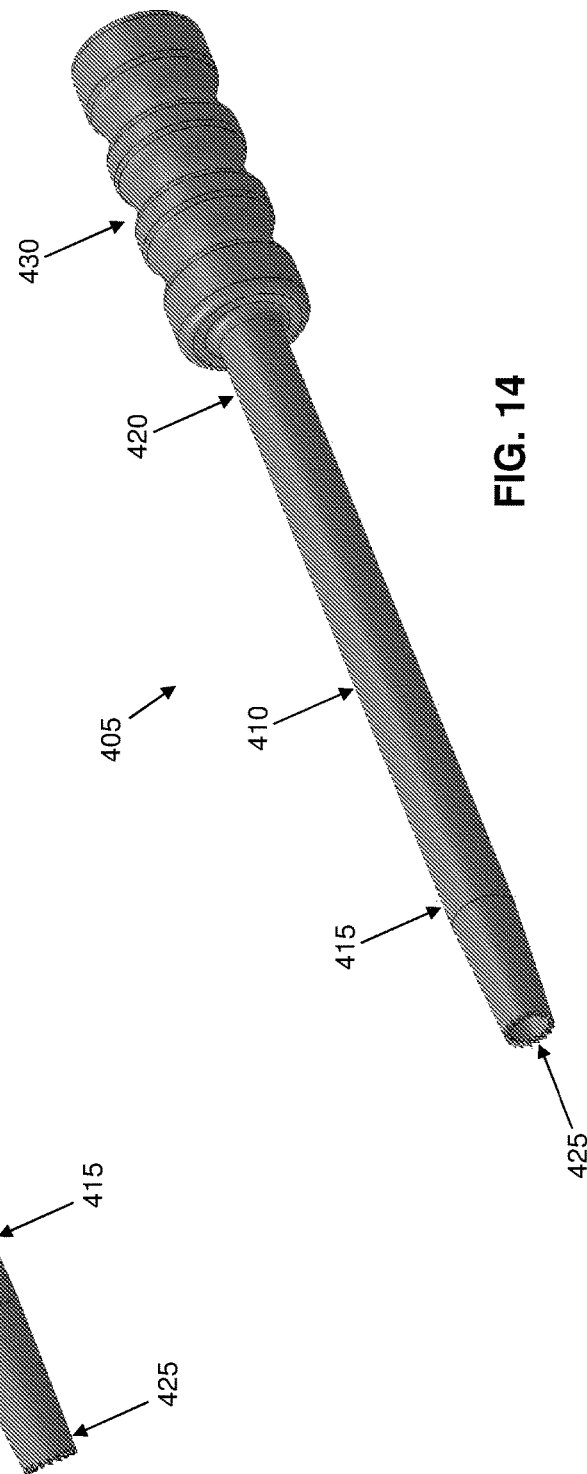

A preferred method for installing novel fusion implant 105 will hereinafter be described. The preferred method for installing novel fusion implant 105 preferably utilizes a joint locator 305 (FIGS. 11 and 12), a joint decorticator 405 (FIGS. 13 and 14), a drill guide/cannula 505 (FIGS. 15-17), and a tamp 605 (FIGS. 18 and 19).

More particularly, joint locator 305 (FIGS. 11 and 12) generally comprises a shaft 310 having a distal end 315 and a proximal end 320. A finger 325 extends distally from distal end 315 of shaft 310.

Joint decorticator 405 (FIGS. 13 and 14) generally comprises a hollow tubular structure 410 having a distal end 415 and a proximal end 420. A cutting element 425 is disposed at distal end 415 of hollow tubular structure 410, and a handle 430 is disposed at proximal end 420 of hollow tubular structure 410.

Drill guide/cannula 505 (FIGS. 15-17) generally comprises a body 510 having a distal end 515 and a proximal end 520. A central lumen 525 extends from distal end 515 to proximal end 520. Central lumen 525 has a cross-sectional profile generally matching a longitudinal projection of the maximum profile of novel fusion implant 105, such that fusion implant 105 can be advanced along the length of central lumen 525 in a controlled sliding motion. More particularly, the cross-sectional profile of central lumen 525 comprises a generally rectangular portion 530 for accommodating body 110 of fusion implant 105, a first generally hemispherical portion 535 for accommodating superior stabilizer 115 of fusion implant 105, and a second generally hemispherical portion 540 for accommodating inferior stabilizer 120 of fusion implant 105.

Drill guide/cannula 505 also comprises a first drill guide lumen 545. First drill guide lumen 545 is oriented at an angle to the longitudinal axis of central lumen 525. Note that the angle at which first drill guide lumen 545 is oriented relative to the longitudinal axis of central lumen 525 is the same angle $\beta$ at which tangent line 235 of inferior stabilizer 120 extends to longitudinal axis 230 of body 110 of fusion implant 105, such that first drill guide lumen 545 can be used to prepare a seat in the ascending facet of a facet joint (e.g., ascending facet 20 of C4 cervical vertebra 25), as will hereinafter be discussed in further detail.

Drill guide/cannula 505 also comprises a second drill guide lumen 550. Second drill guide lumen 550 is oriented at an angle to the longitudinal axis of central lumen 525. Note that the angle at which second drill guide lumen 550 is oriented relative to the longitudinal axis of central lumen 525 is the same angle $\alpha$ at which tangent line 225 of superior stabilizer 115 extends to longitudinal axis 230 of body 110 of fusion implant 105, such that second drill guide lumen 550 can be used to prepare a seat in the descending facet of a facet joint (e.g., descending facet 10 of C3 cervical vertebra 15), as will hereinafter be discussed in further detail.

Drill guide/cannula 505 also comprises a pair of fingers 555 extending distally from its distal end 515. Note that fingers 555 are aligned in a first plane 560 (FIG. 15) which extends perpendicular to a second plane 565 (FIG. 17) which passes through first drill guide lumen 545 and second drill guide lumen 550 so that, when fingers 555 are inserted into the gap in the facet joint (see below), first drill guide lumen 545 and second drill guide lumen 550 may be used to prepare seats in the descending facet of a facet joint, and the ascending facet of a facet joint, respectively (as will hereinafter be discussed). Note also that the aforementioned second plane 565 bisects first generally hemispherical portion 535 of central lumen 525 and second generally hemispherical portion 540 of central lumen 525 so that, when fingers 555 are inserted into the gap in the facet joint (see below), first generally hemispherical portion 535 and second generally hemispherical portion 540 may be used to orient fusion implant 105 relative to the seats previously prepared in the descending facet of a facet joint, and the ascending facet of a facet joint, respectively (as will hereinafter be discussed).

Tamp 605 (FIGS. 18 and 19) comprises a shaft 610 having a distal end 615 and a proximal end 620. Shaft 610 preferably has a rectangular cross-section similar to generally rectangular portion 530 of central lumen 525 of drill guide/cannula 505. A finger 625 extends distally from distal end 615 of shaft 610. An impactor extension 630 is mountable to proximal end 620 of shaft 610, such that hammering on the proximal end of impactor extension 630 will transmit distally-directed force to shaft 610. A superior projection 635 is disposed on shaft 610 just proximal to finger 625. Superior projection 635 has a hemispherical cross-section similar to first generally hemispherical portion 535 of central lumen 525 of drill guide/cannula 505. As a result of this construction, tamp 605 can make a close sliding fit within central lumen 525 of drill guide/cannula 505, whereby to enable tamp 605 to advance fusion implant 105 along the length of central lumen 525, as will hereinafter be discussed. In addition, when impactor extension 630 is mounted to proximal end 620 of shaft 610, hammering on the proximal end of impactor extension 630 will transmit distally-directed force to shaft 610 of tamp 605, whereby to transmit distally-directed force to fusion implant 105, as will hereinafter be discussed.

Preferred Method for Installing the Novel Fusion Implant

First, the facet joint is visualized by the surgeon, either indirectly by imaging the patient (e.g., by fluoroscopy) or directly by visualization during an open procedure.

Figure 20:
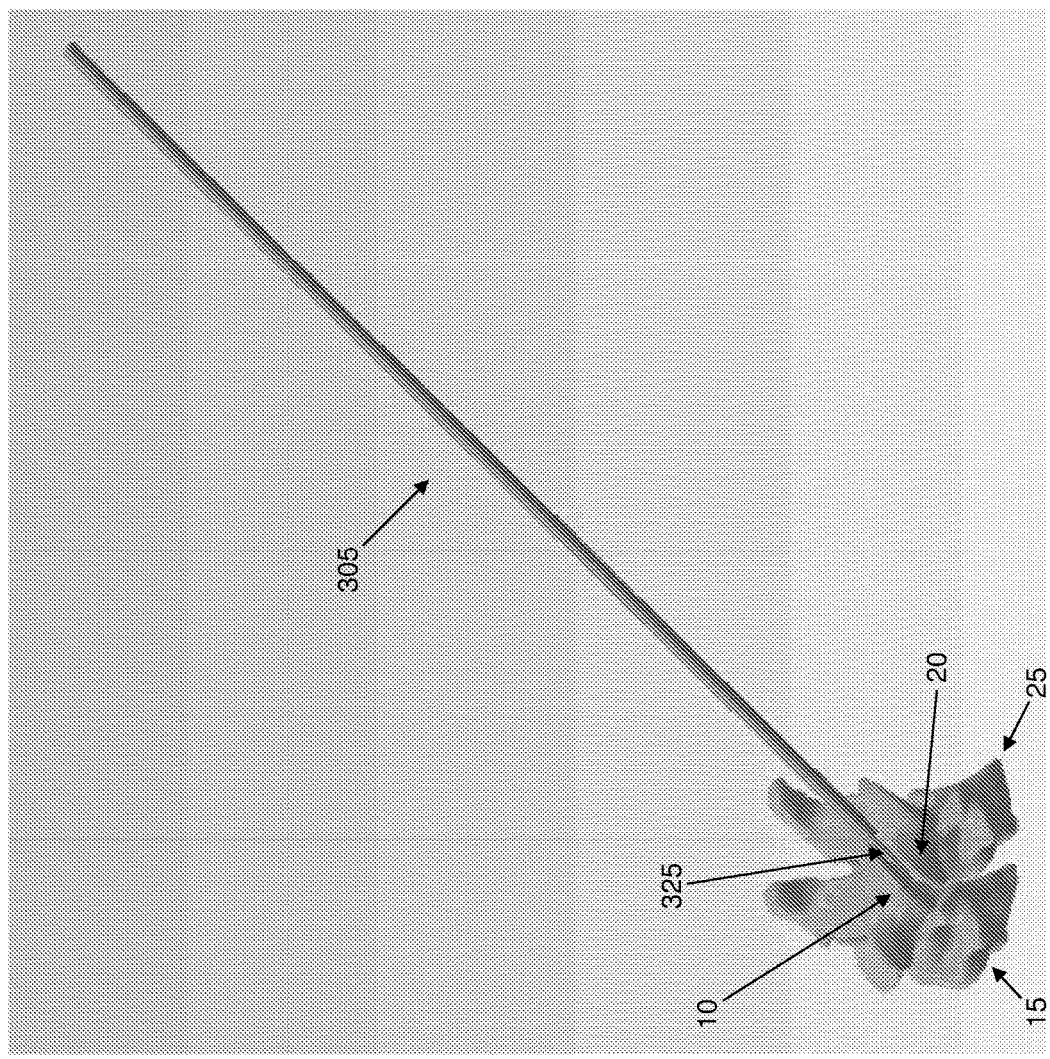
Figure 21:
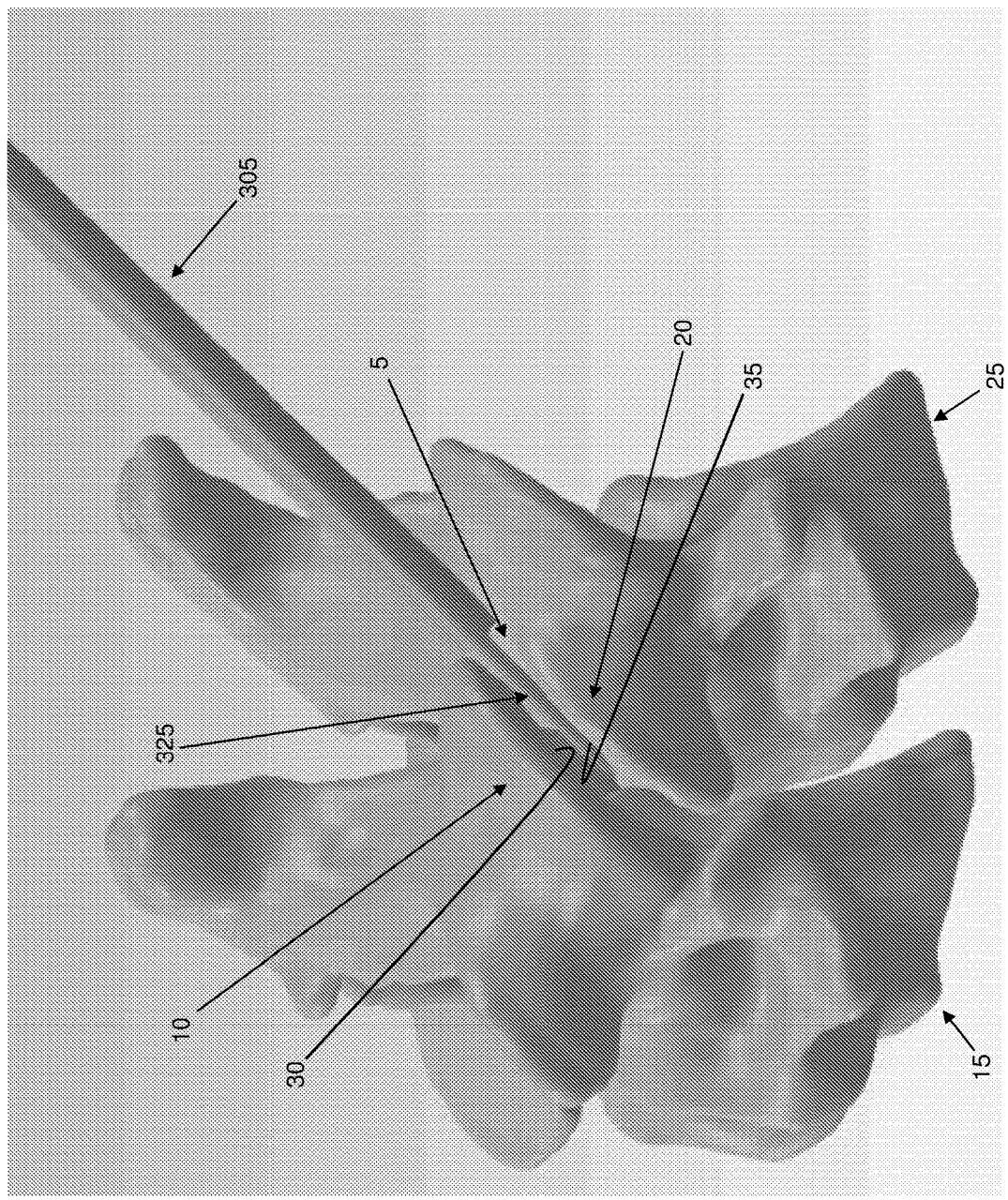
Figure 21A:
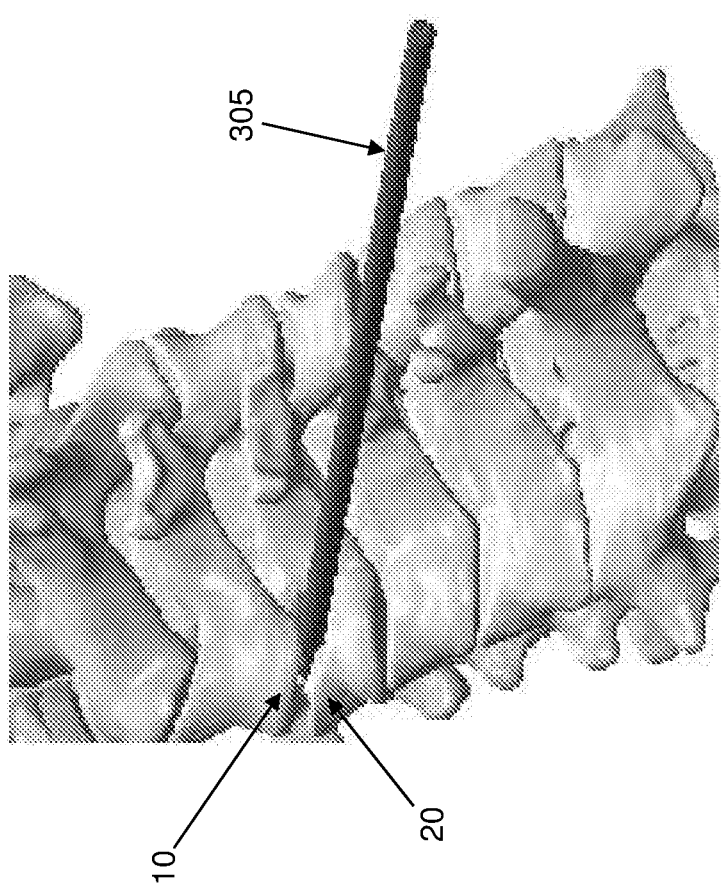

Next, and looking now at FIGS. 20, 21 and 21A, joint locator 305 is inserted into the gap between the opposing facet surfaces (e.g., between face 30 of descending facet 10 of C3 cervical vertebrae 15 and face 35 of ascending facet 20 of C4 cervical vertebrae 25). More particularly, finger 325 of joint locator 305 is advanced into the gap between the opposing facet surfaces and then the position of joint locator 305 is verified, e.g., by viewing along the coronal and sagittal planes of the patient. After verification is complete, the proximal end of joint locator 305 is lightly tapped so as to advance finger 325 of joint locator 305 further into the facet joint, until distal end 315 of shaft 310 engages the outer surfaces of the facets. At this point, joint locator 305 is essentially fixed to the facet joint and provides a "track" to the facet joint.

Figure 22:
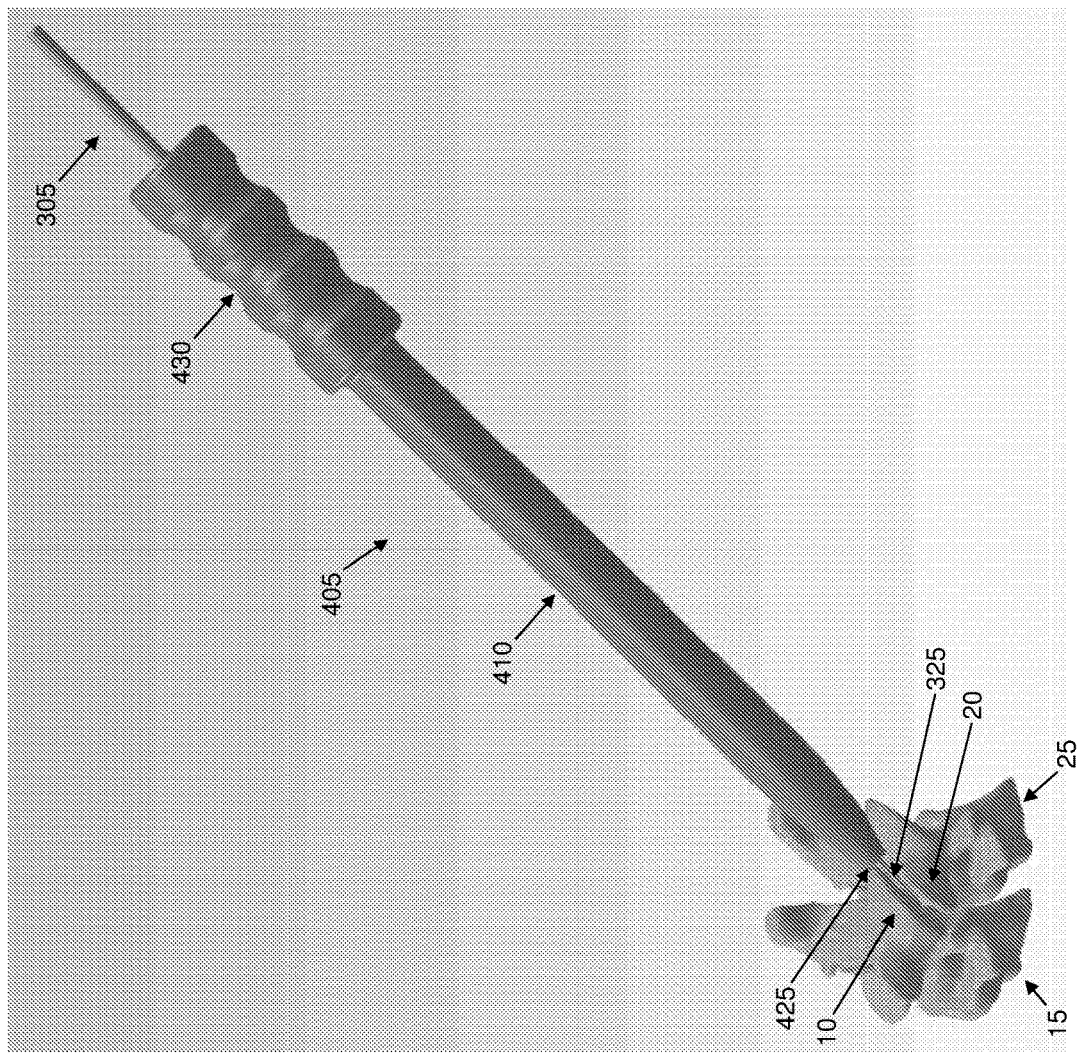
Figure 23:
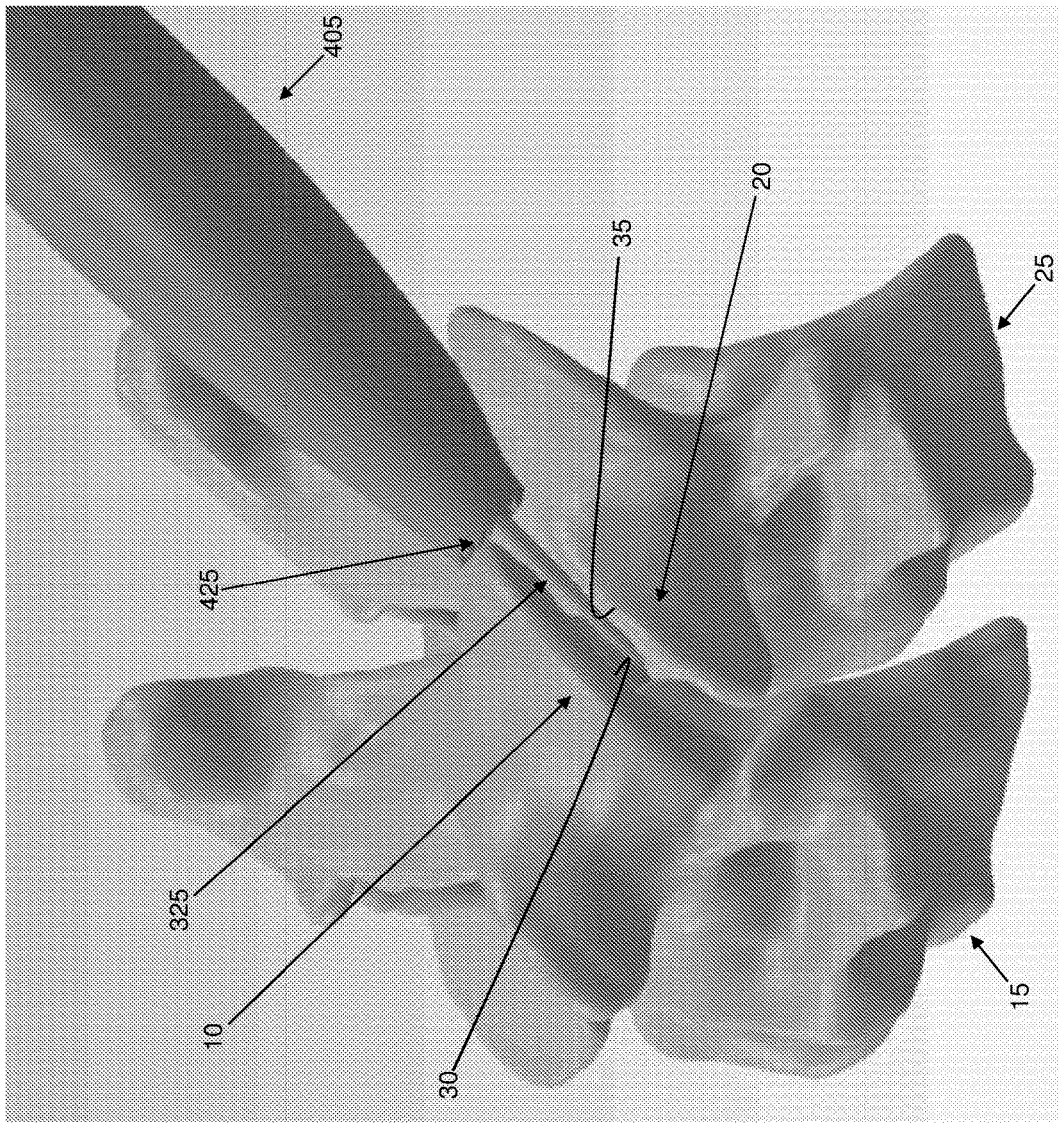
Figure 23A:
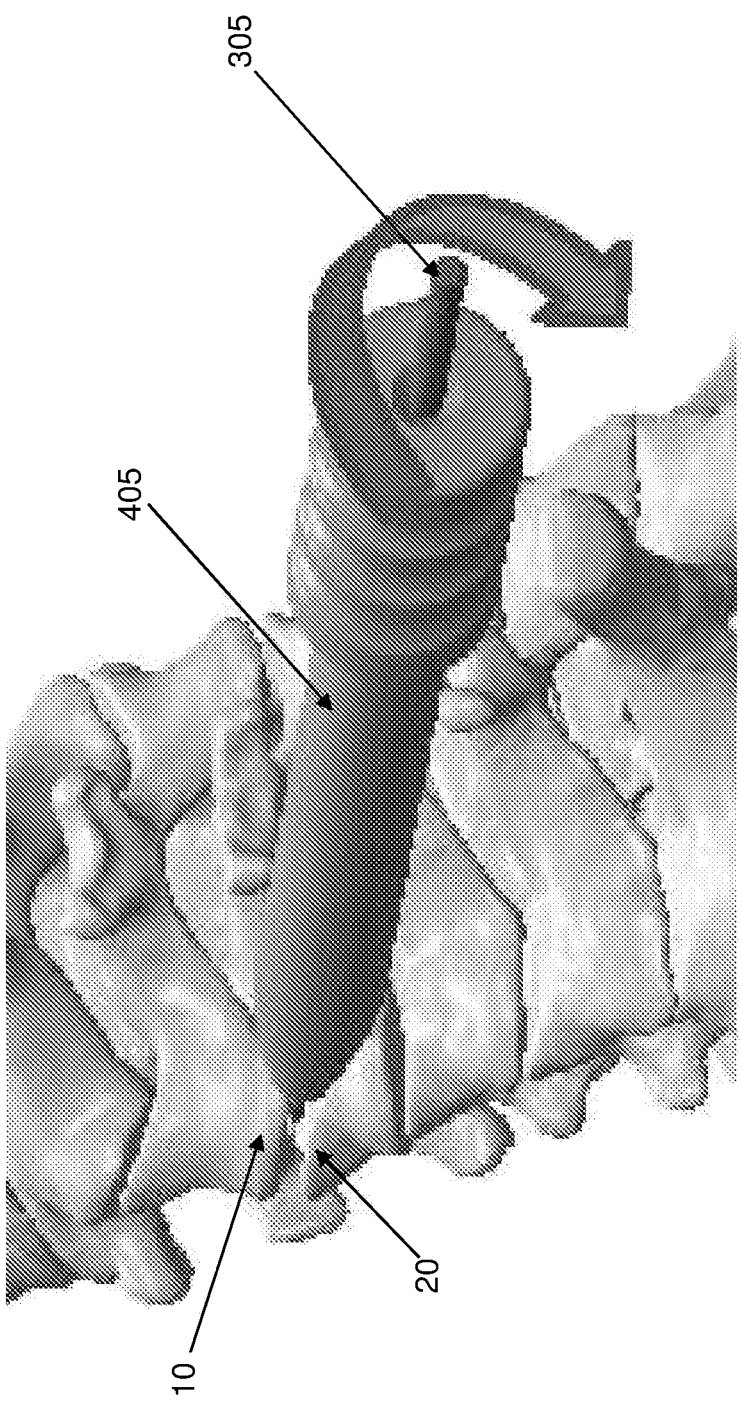

Next, and looking now at FIGS. 22, 23 and 23A, joint decorticator 405 is slid over joint locator 305 so that the joint decorticator is aligned with the gap between the opposing facet surfaces (e.g., between face 30 of descending facet 10 of C3 cervical vertebrae 15 and face 35 of ascending facet 20 of C4 cervical vertebrae 25). Then joint decorticator 405 is used to decorticate the ends of the opposing facets. After decortication is completed, joint decorticator 405 is removed from joint locator 305.

Then, and looking now at FIG. 24, drill guide/cannula 505 is advanced over joint locator 305 (i.e., by fitting the distal end of central lumen 525 of drill guide/cannula 505 over proximal end 320 of joint locator 305, and then advancing the drill guide/cannula distally along joint locator 305). Drill guide/cannula 505 is advanced distally along joint locator 305 until fingers 555 of drill guide/cannula 505 enter the gap between the opposing facets. Then fingers 555 of drill guide/cannula 505 are driven into the gap between the opposing facets, whereby to secure drill guide/cannula 505 to the facet joint.

Figure 26A:
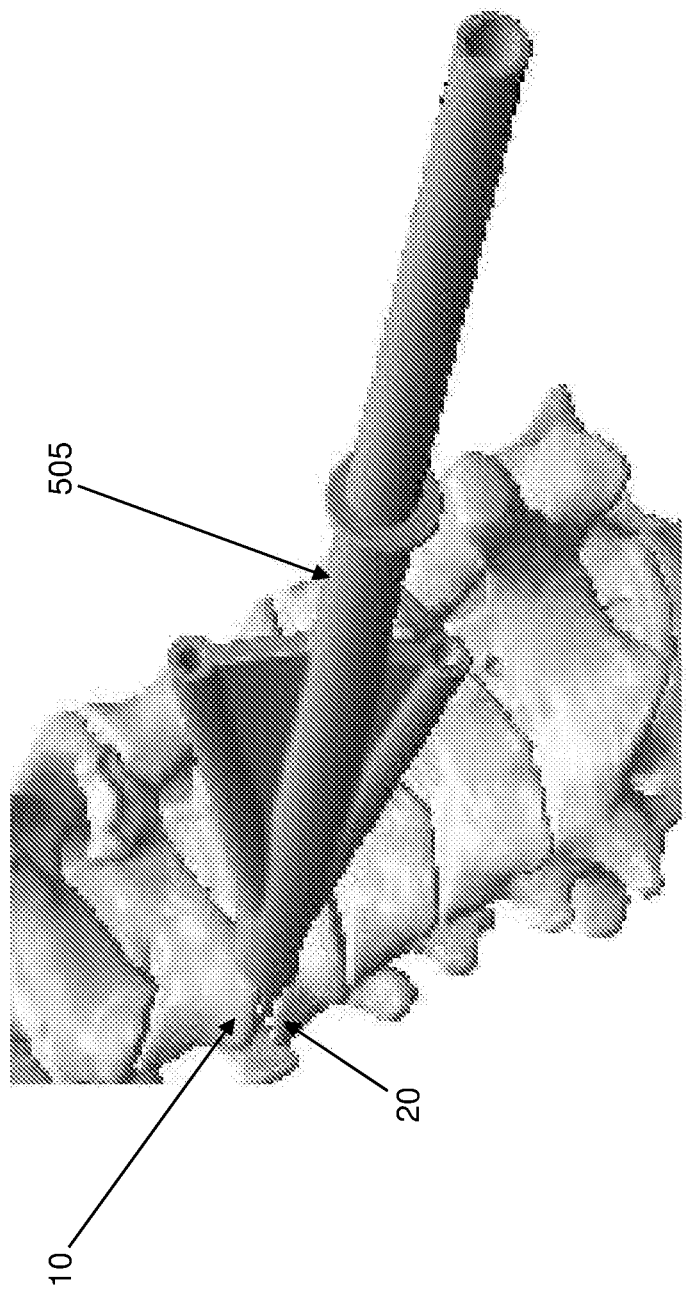

Next, and looking now at FIGS. 25, 26 and 26A, joint locator 305 is removed, e.g., by pulling the joint locator proximally out of central lumen 525 of the facet joint and out of drill guide/cannula 505.

Figure 27:
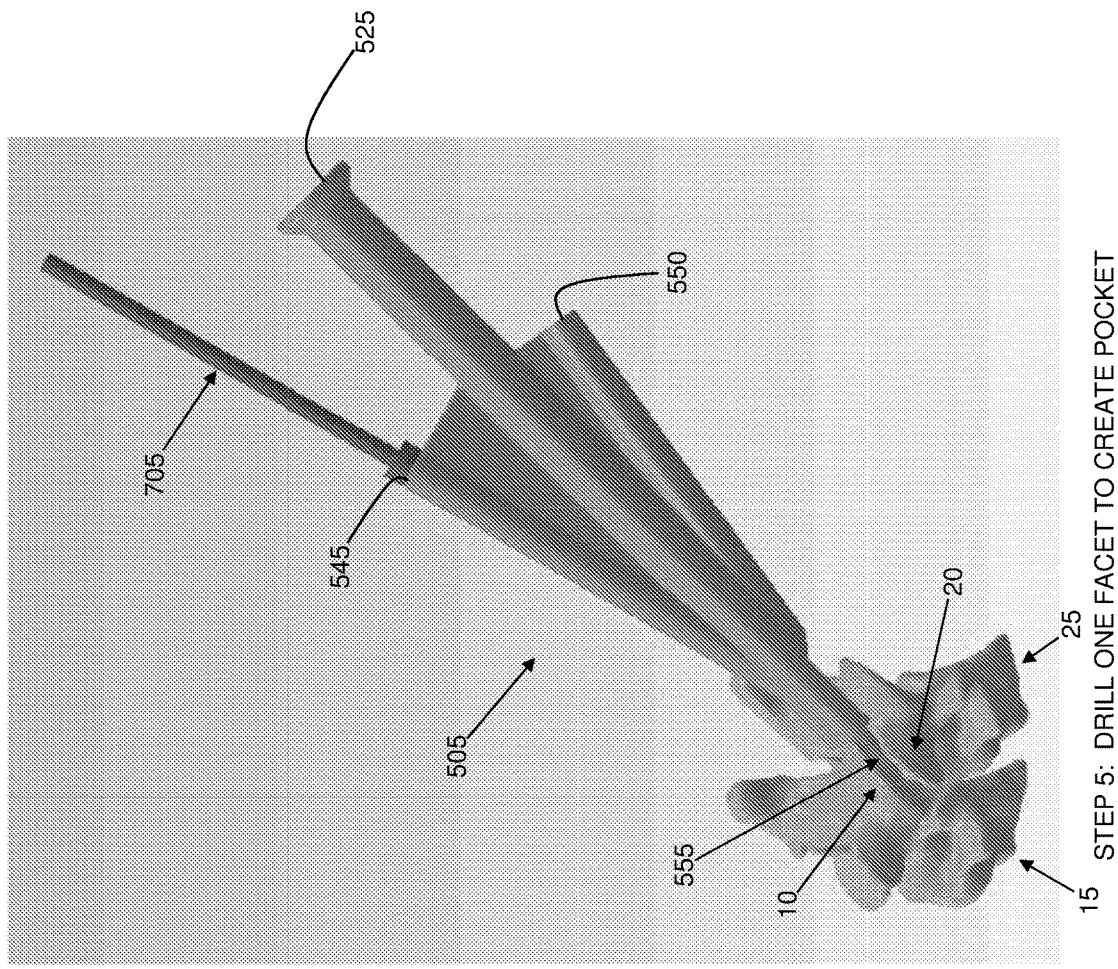
Figure 28:
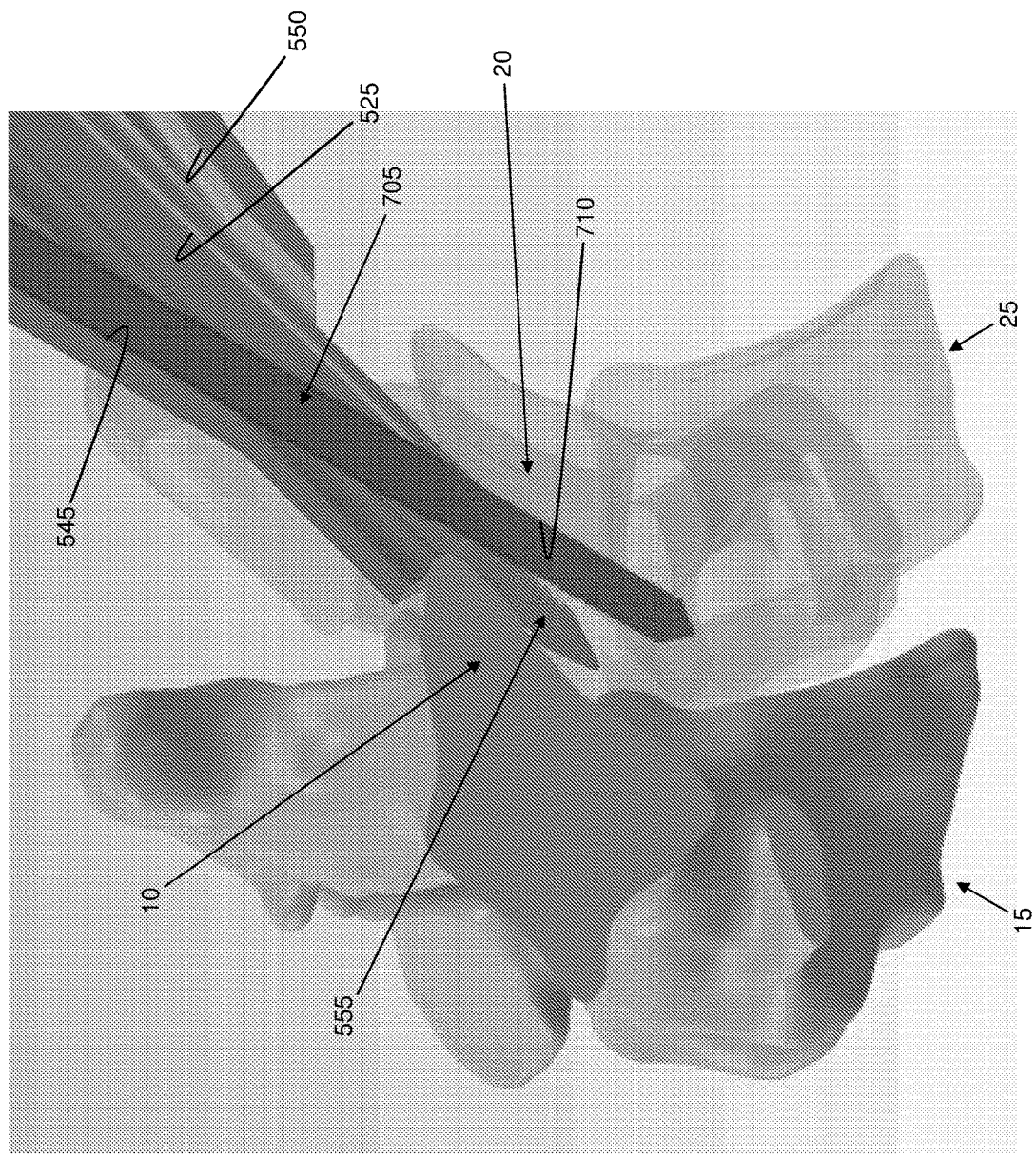

At this point, and looking now at FIGS. 27 and 28, a drill 705 is inserted into first drill guide lumen 545 of drill guide/cannula 505 and advanced into the ascending facet of the facet joint (e.g., ascending facet 20 of C4 cervical vertebrae 25) so as to create a recess 710 in the ascending facet of the facet joint. Recess 710 will subsequently receive inferior stabilizer 120 of fusion implant 105, as will hereinafter be discussed. Then drill 705 is removed from first drill guide lumen 545.

Figure 29:
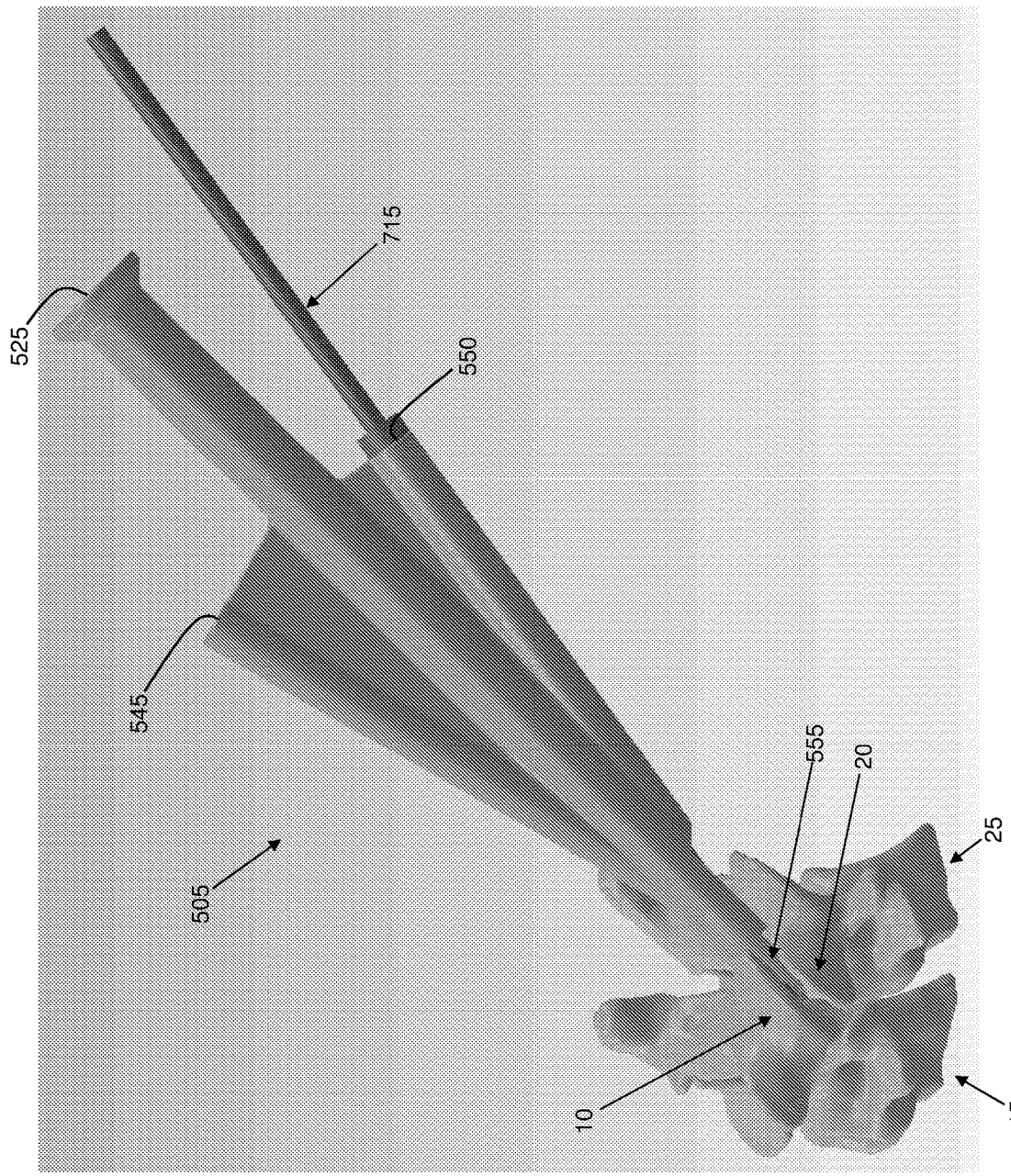

Next, and looking now at FIGS. 29 and 30, a drill 715 (which may or may not be the same as the aforementioned drill 705) is inserted into second drill guide lumen 550 of drill guide/cannula 505 and advanced into the descending facet of the facet joint (e.g., descending facet 10 of C3 cervical vertebrae 15) so as to create a recess 720 in the descending facet of the facet joint. Recess 720 will subsequently receive superior stabilizer 115 of fusion implant 105, as will hereinafter be discussed. Then drill 715 is removed from second drill guide lumen 550.

At this point, and looking now at FIG. 31, a pocket 725 will have been created in the facet joint, i.e., by forming recess 710 in the ascending facet of the facet joint and forming recess 720 in the descending facet of the facet joint. Note that pocket 725 is generally characterized by a superior anterior stop surface 730, an inferior anterior stop surface 735, a superior posterior stop surface 740 and an inferior posterior stop surface 745.

Next, and looking now at FIGS. 32-36, fusion implant 105 is installed into the facet joint using drill guide/cannula 505 and tamp 605.

More particularly, fusion implant 105 is inserted into the proximal end of central lumen 525 of drill guide/cannula 505 (FIGS. 31 and 32) so that body 110 of fusion implant 105 is received in generally rectangular portion 530 of central lumen 525, superior stabilizer 115 of fusion implant 105 is received in first generally hemispherical portion 535 of central lumen 525, and inferior stabilizer 120 is received in second generally hemispherical portion 540 of central lumen 525.

Then tamp 605 is used to advance fusion implant 105 along central lumen 525 of drill guide/cannula 505, and then tamp 605 and impactor extension 630 are used to hammer fusion implant 105 into the aforementioned pocket 725 formed in the facet joint (FIGS. 33-36), with body 110 of fusion implant 105 spanning the gap between the descending facet of the facet joint and the ascending facet of the facet joint, and with superior stabilizer 115 of fusion implant 105 being received in recess 720 in the descending facet of the facet joint, and with inferior stabilizer 120 of fusion implant 105 being received in recess 710 in the ascending facet of the facet joint, whereby to immobilize the facet joint and facilitate fusing of the facet joint. After fusion implant 105 is installed in pocket 725 in the facet joint, tamp 605 and drill guide/cannula 505 are removed from the surgical site, thereby completing the installation of fusion implant 105 into the facet joint.

Figure 32A:
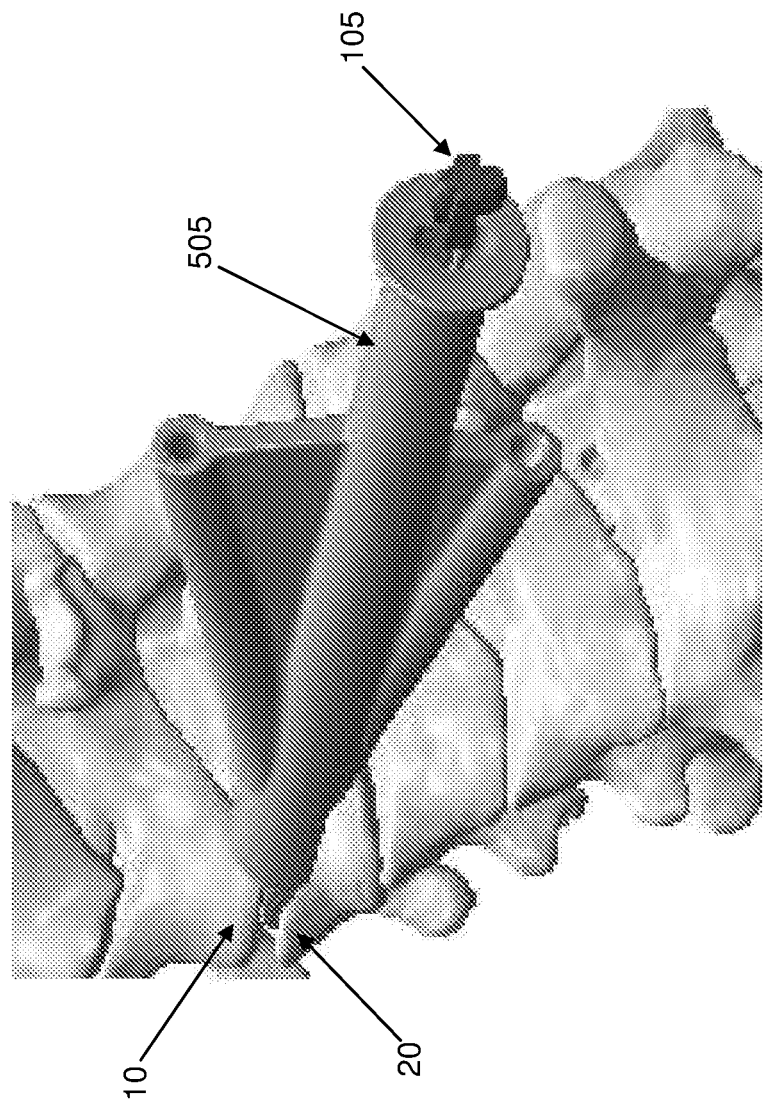
Figure 34:
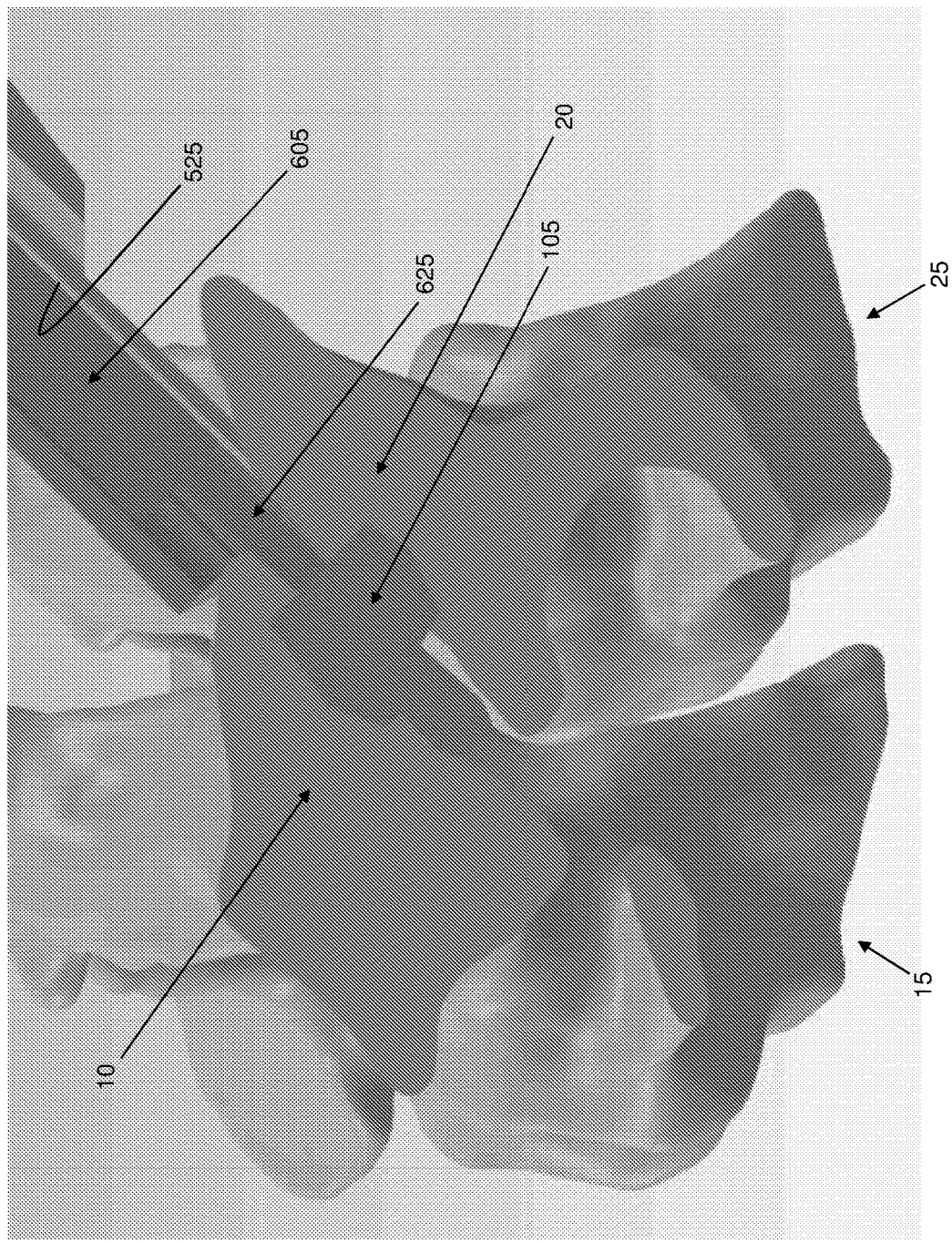
Figure 35:
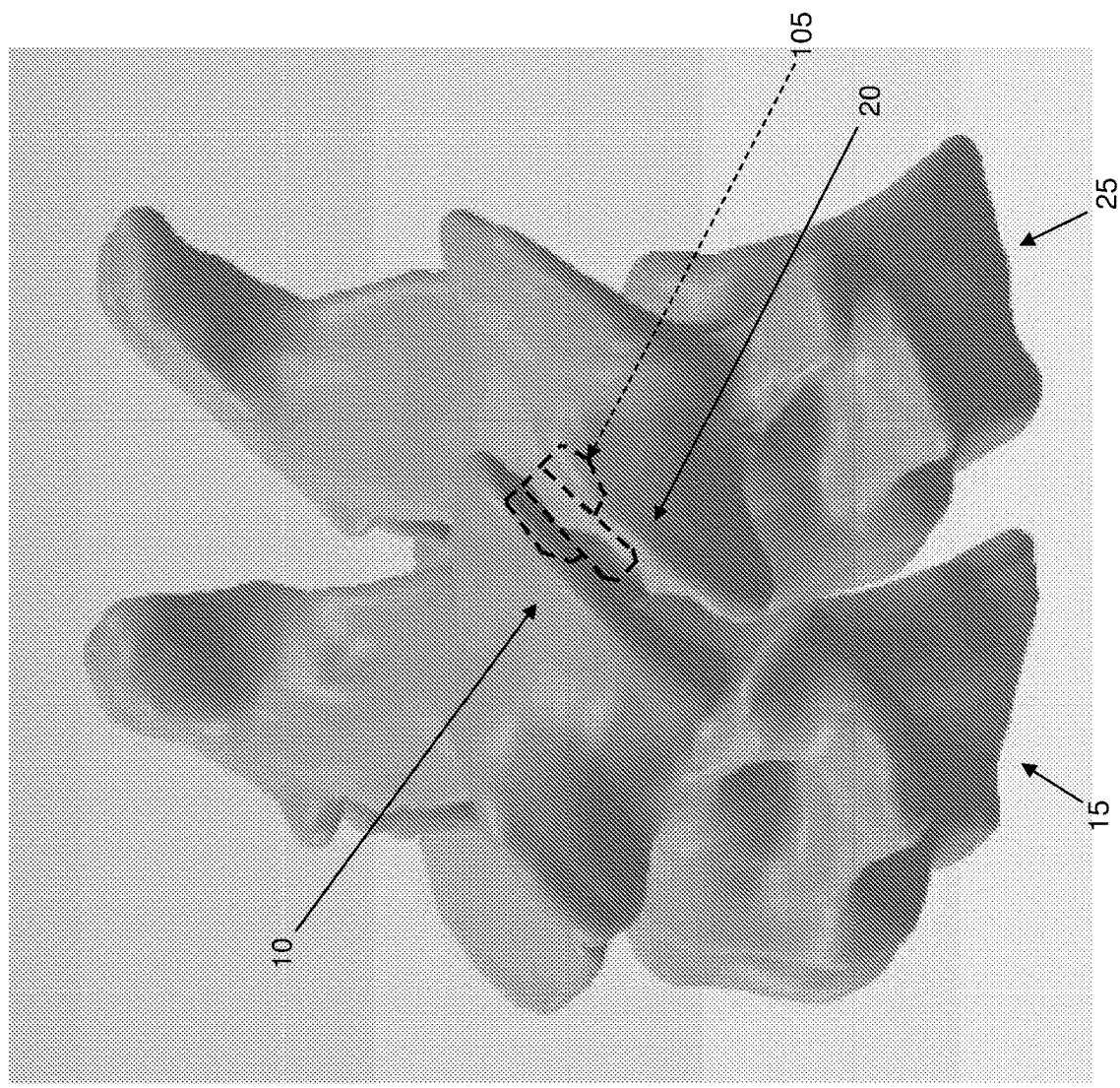
Figure 36:
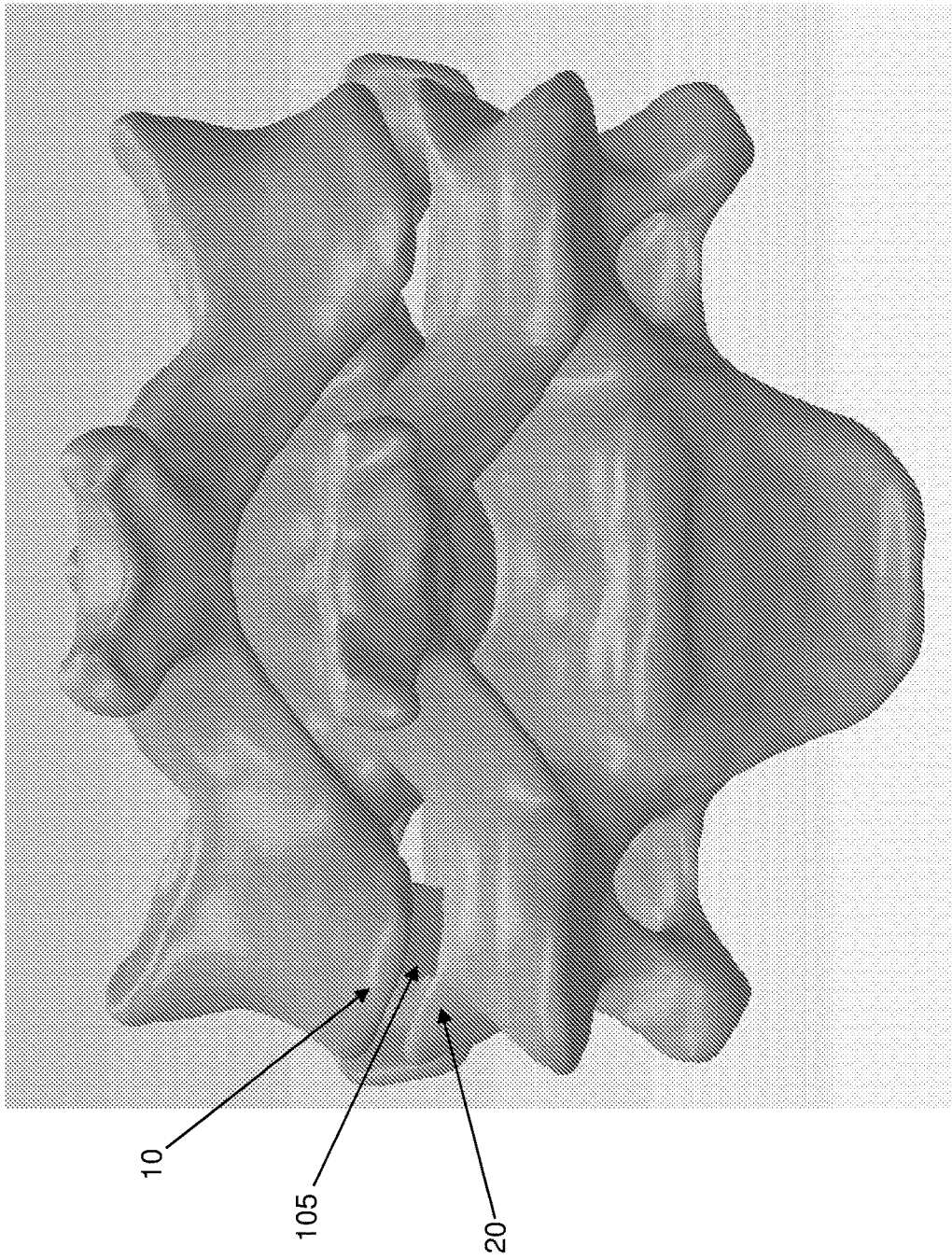
Figure 36A:
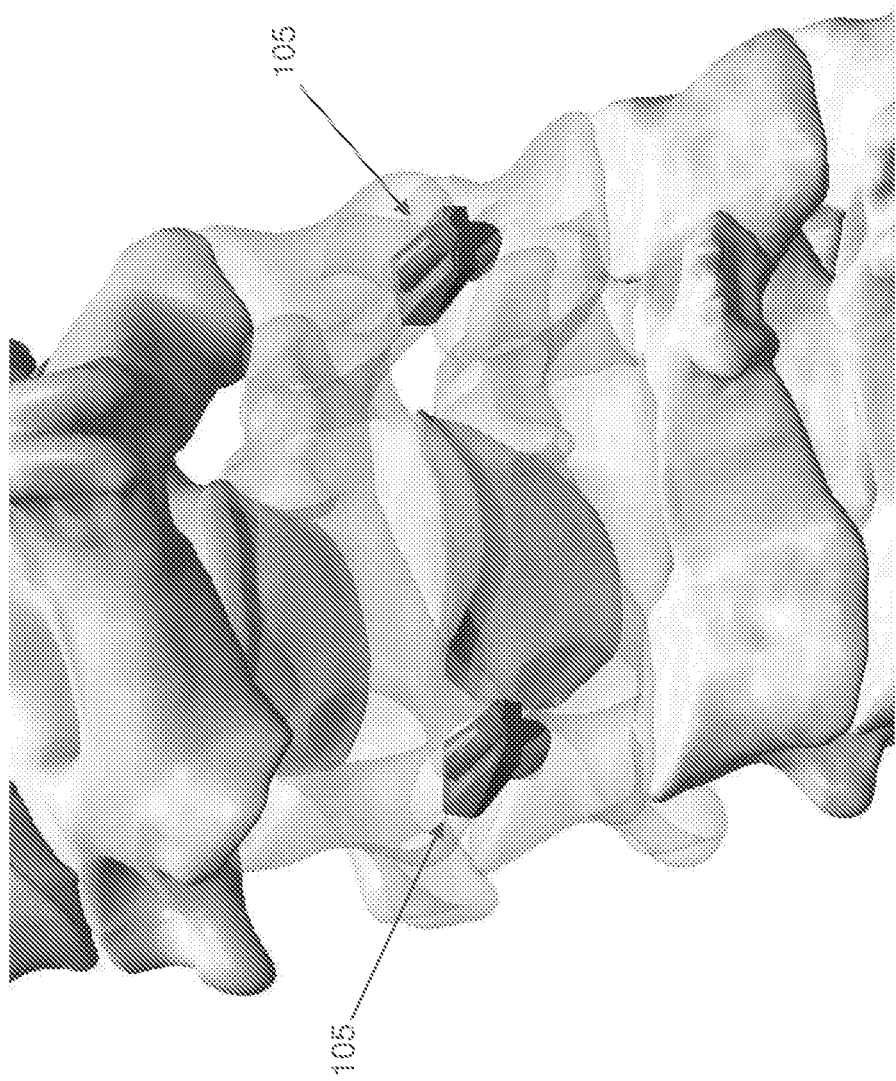
FIG. 36A is a schematic view showing two novel fusion implants of FIGS. 5-10 installed in a pair of facet joints.

FIG. 32A shows two fusion implants 105 disposed in two facet joints in a spine.

Figure 37:
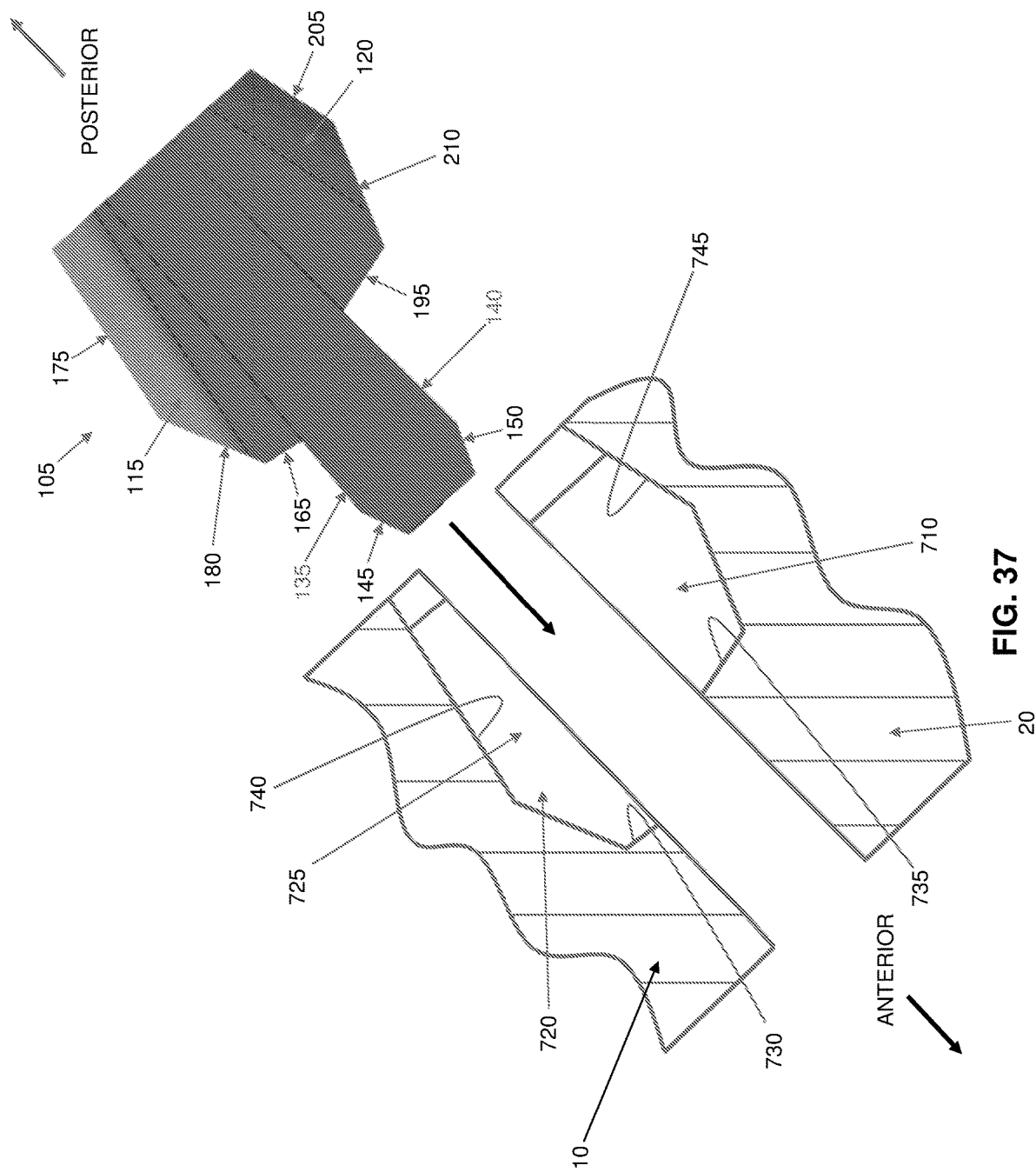
FIG. 37 is a schematic view showing how the novel fusion implant of FIGS. 5-10 interacts with the opposing facets of two adjacent cervical vertebrae so as to immobilize the facet joint and facilitate fusion between the opposing facets.

Significantly, and looking now at FIG. 37, inasmuch as fusion implant 105 is configured to be "taller" at its distal end than at its proximal end, and inasmuch as fusion implant 105 is configured to have a "height" at its proximal end which is approximately the same as the "height" of the gap between the two facets of the facet joint, the two facets are distracted somewhat during insertion of the fusion implant into the aforementioned pocket 725. As fusion implant 105 settles into pocket 725, the facets are able to return toward their undistracted condition and compress back against the fusion implant, essentially creating something of a "friction fit" between fusion implant 105 and the two facets of facet joint 5. By forming fusion implant 105 with angled surfaces, and by forming the aforementioned pocket 725 in the facets with angled surfaces, the fusion implant is prevented from moving anteriorly or posteriorly once the facets have compressed back into their normal disposition. More particularly, movement of fusion implant 105 in the anterior direction is prevented by engagement of superior stabilizer 115 and inferior stabilizer 120 with superior anterior stop surface 730 of pocket 725 and inferior anterior stop surface 735 of pocket 725, respectively. Movement of fusion implant 105 in the posterior direction is prevented by engagement of superior stabilizer 115 and inferior stabilizer 120 with superior posterior stop surface 740 of pocket 725 and inferior posterior stop surface 745 of pocket 725, respectively. Thus it will be appreciated that, in order for superior stabilizer 115 and inferior stabilizer 120 to pass by superior posterior stop surface 740 and inferior posterior stop surface 745, respectively, the facet joint would have to over-distract, which is inhibited by the surrounding soft tissue structure.

By way of example but not limitation, where fusion implant 105 is to be seated between the C3 cervical vertebra and the C4 cervical vertebra (FIG. 37), as fusion implant 105 is advanced into the gap between face 30 of descending facet 10 of C3 cervical vertebra 15 and face 35 of ascending facet 20 of C4 cervical vertebra 25, superior beveled surface 145 of fusion implant 105 and inferior beveled surface 150 of fusion implant 105 will engage descending facet 10 of C3 cervical vertebra 15 and ascending facet 20 of C4 cervical vertebra 25, respectively, and cam the two facets apart. Further insertion of fusion implant 105 into the facet joint causes superior beveled surface 180 of superior stabilizer 115 and inferior beveled surface 210 of inferior stabilizer 120 to engage descending facet 10 of C3 cervical vertebra 15 and ascending facet 20 of C4 cervical vertebra 25, respectively, and cam the two facets further apart. As fusion implant 105 settles into pocket 725, face 30 of descending facet 10 of C3 cervical vertebra 15 settles against superior surface 135 of body 110, face 35 of ascending facet 20 of C4 cervical vertebra 25 settles against inferior surface 140 of body 110, superior anterior stop surface 730 of pocket 725 settles against distal end surface 165 of superior stabilizer 115, inferior anterior stop surface 735 of pocket 725 settles against distal end surface 195 of inferior stabilizer 120, superior posterior stop surface 740 of pocket 725 settles against rounded superior surface 175 of superior stabilizer 115 and inferior posterior stop surface 745 of pocket 725 settles against rounded inferior surface 205 of inferior stabilizer 120, whereby to lock fusion implant 105 against anterior or posterior movement.

Additionally, the wedge-like construction of fusion implant 105 creates/restores lordosis.

In the preferred form of the invention, descending facet 10 contacts, and is supported by, superior beveled surface 145, superior surface 135, distal end surface 165, superior beveled surface 180 and rounded superior surface 175 of fusion implant 105; and ascending facet 20 contacts, and is supported by, inferior beveled surface 150, inferior surface 140, distal end surface 195, inferior beveled surface 210 and rounded inferior surface 205 of fusion implant 105.

However, if desired, in another form of the invention, descending facet 10 contacts, and is supported by, less than all of the aforementioned superior beveled surface 145, superior surface 135, distal end surface 165, superior beveled surface 180 and rounded superior surface 175 of fusion implant 105; and ascending facet 20 contacts, and is supported by, less than all of the aforementioned inferior beveled surface 150, inferior surface 140, distal end surface 195, inferior beveled surface 210 and rounded inferior surface 205 of fusion implant 105. By way of example but not limitation, in another form of the invention, descending facet 10 contacts, and is supported by, only superior surface 135 of fusion implant 105 and ascending facet 20 contacts, and is supported by, only inferior surface 140 of fusion implant 105. By way of further example but not limitation, in another form of the invention, descending facet 10 contacts, and is supported by, only rounded superior surface 175 of fusion implant 105 and ascending facet 20 contacts, and is supported by, only rounded inferior surface 205 of fusion implant 105.

Alternative Constructions

Figure 38:
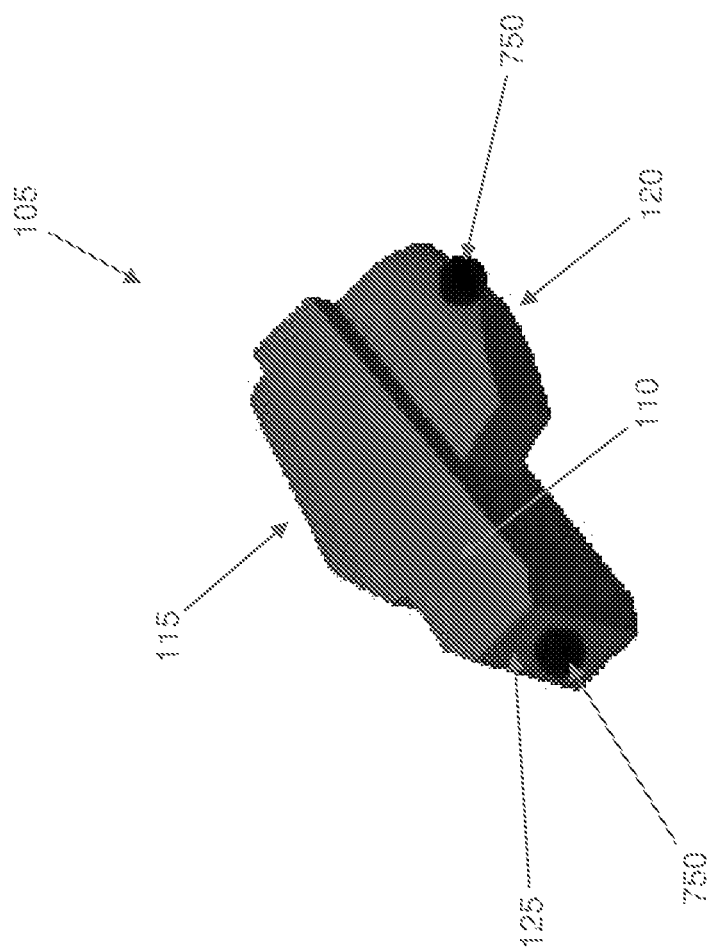
FIGS. 38-42 are schematic views showing additional novel fusion implants formed in accordance with the present invention.

If desired, fusion implant 105 may comprise visual markers to facilitate proper orientation of the fusion implant when fusion implant 105 is inserted into the proximal end of central lumen 525 of drill guide/cannula 505. By way of example but not limitation, and looking now at FIG. 38, fusion implant 105 may comprise a black dot 750 on one or both of inferior stabilizer 120 (e.g., to identify the inferior side of fusion implant 105) and/or distal end surface 125 of body 110 (e.g., to identify the distal end of fusion implant 105).

The configuration of fusion implant 105 may be varied without departing from the scope of the present invention.

By way of example but not limitation, it should be appreciated that the new fusion implant may be manufactured in a wide range of different sizes in order to accommodate any size of facet joint.

Furthermore, the scale and aspect ratio of body 110, superior stabilizer 115 and inferior stabilizer 120 may all be varied without departing from the scope of the present invention.

Figure 39:
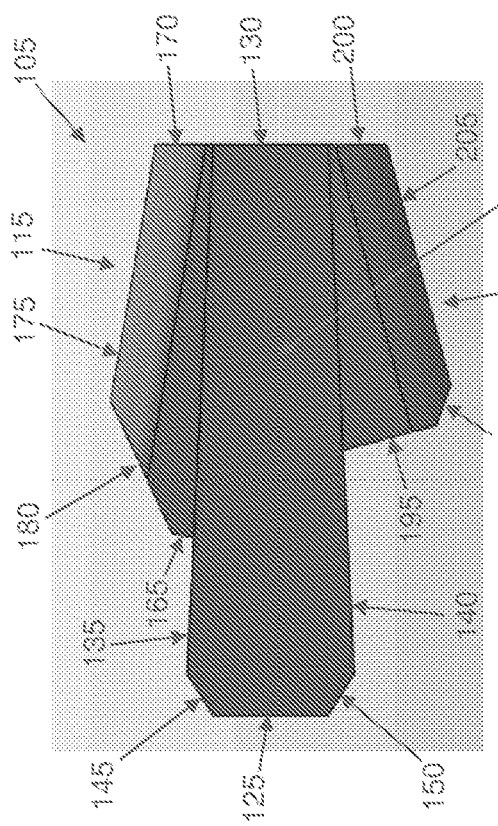

See, for example, FIG. 39, which shows a fusion implant 105 wherein the configurations of superior stabilizer 115 and inferior stabilizer 120 differ from the configurations of superior stabilizer 115 and inferior stabilizer 120 in the fusion implant 105 shown in FIGS. 5-10.

By way of further example but not limitation, fusion implant 105 may be formed so that superior stabilizer 115 and inferior stabilizer 120 have identical configurations.

Figure 40:
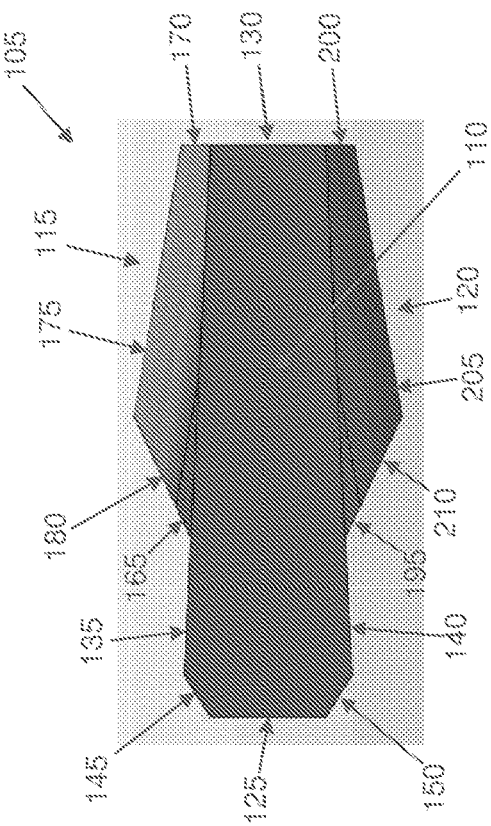

See, for example, FIG. 40, where superior stabilizer 115 and inferior stabilizer 120 have identical configurations (and where those configurations vary from the configurations of superior stabilizer 115 and inferior stabilizer 120 in the fusion implant 105 shown in FIGS. 5-10).

Figure 41:
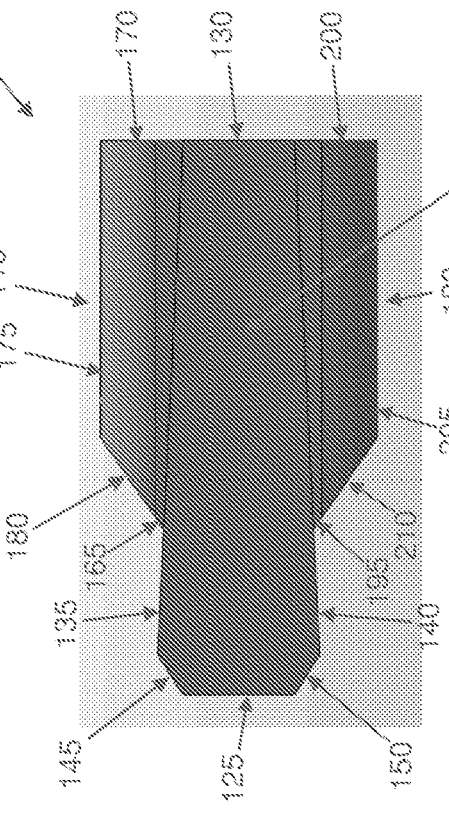

See also, for example, FIG. 41, where the apexes of rounded superior surface 175 of superior stabilizer 115 and rounded inferior surface 205 of inferior stabilizer 120 extend substantially parallel to one another.

Figure 42:
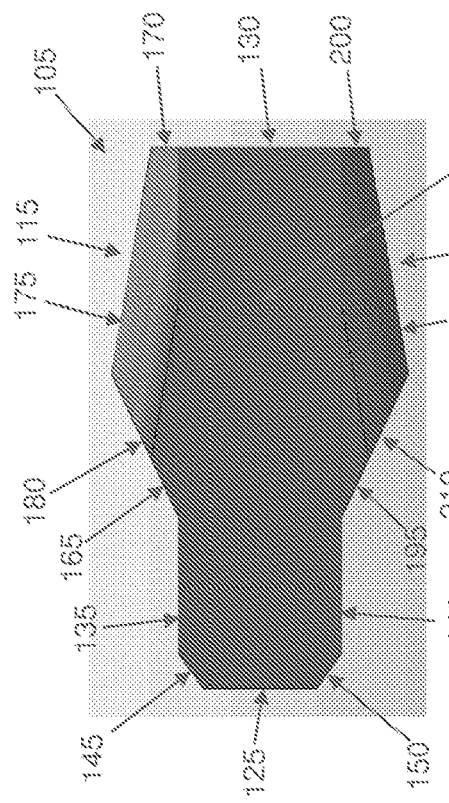

And see, for example, FIG. 42, where superior surface 135 and inferior surface 140 of body 110 extend substantially parallel to one another.

It will, of course, be appreciated that the configuration of drill guide/cannula 505 may change as the configuration of fusion implant 105 changes in order to (i) enable drill guide/cannula 505 to create an appropriate pocket 725 in the facet joint, and (ii) enable drill guide/cannula 505 to provide an appropriate channel for advancing fusion implant 105 into pocket 725 in the facet joint.

Additionally, the new fusion implant may be constructed out of any substantially biocompatible material which has properties consistent with the present invention including, but not limited to, allograft, autograft, synthetic bone, simulated bone material, biocomposites, ceramics, PEEK, stainless steel and titanium. Thus, the present invention permits the surgeon to select a fusion implant having the appropriate size and composition for a given facet fusion.

Advantages of the Invention

Numerous advantages are achieved by the present invention. Among other things, the present invention provides a fast, simple, minimally-invasive, easily reproduced and highly effective approach for effecting facet fusion, particularly with cervical facet joints. The fusion implant is able to withstand greater forces, prohibit motion in all directions and drastically reduce the risk of implant failure. The fusion implant also eliminates the possibility of slippage during spinal motion, greatly improves facet stability and promotes better facet fusion.

Applications to Joints Other than Facet Joints

While fusion implant 105 has been discussed above in the context of fusing a facet joint, it should also be appreciated that fusion implant 105 may be used to stabilize and fuse any joint having anatomy similar to the facet joint, i.e., a pair of opposing bony surfaces defining a gap therebetween, with the stabilizer of the fusion implant being sized to be positioned within the gap. By way of example but not limitation, the fusion implant may be used in small joints such as the fingers, toes, etc.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A spinal facet fusion implant comprising:
    an elongated body having a distal end, a proximal end and a longitudinal axis extending between the distal end and the proximal end, the elongated body being characterized by a superior body surface and an inferior body surface;
    a superior stabilizer extending outwardly from the superior body surface, the superior stabilizer being characterized by a superior stabilizer surface; and
    an inferior stabilizer extending outwardly from the inferior body surface, the inferior stabilizer being characterized by an inferior stabilizer surface;
    wherein (i) the superior body surface and the inferior body surface are tapered relative to one another, and/or (ii) the superior stabilizer surface and the inferior stabilizer surface are tapered relative to one another;
    wherein the elongated body comprises a proximal end surface, the superior stabilizer comprises a proximal end surface, and the inferior stabilizer comprises a proximal end surface, and further wherein the proximal end surface of the elongated body, the proximal end surface of the superior stabilizer, and the proximal end surface of the inferior stabilizer are all co-planar.

2. A spinal facet fusion implant according to claim 1 wherein the superior body surface and the inferior body surface are tapered relative to one another.

3. A spinal facet fusion implant according to claim 1 wherein the superior body surface and the inferior body surface are tapered inwardly relative to one another in a proximal direction.

4. A spinal facet fusion implant according to claim 3 wherein the superior stabilizer surface and the inferior stabilizer surface extend parallel to one another.

5. A spinal facet fusion implant according to claim 1 wherein the superior stabilizer surface and the inferior stabilizer surface are tapered relative to one another.

6. A spinal facet fusion implant according to claim 1 wherein the superior stabilizer surface and the inferior stabilizer surface are tapered inwardly relative to one another in a proximal direction.

7. A spinal facet fusion implant according to claim 6 wherein the superior body surface and the inferior body surface extend parallel to one another.

8. A spinal facet fusion implant according to claim 1 wherein the superior body surface and the inferior body surface are tapered relative to one another, and wherein the superior stabilizer surface and the inferior stabilizer surface are tapered relative to one another.

9. A spinal facet fusion implant according to claim 8 wherein the superior body surface and the inferior body surface are tapered inwardly relative to one another in the proximal direction, and wherein the superior stabilizer surface and the inferior stabilizer surface are tapered inwardly relative to one another in a proximal direction.

10. A spinal facet fusion implant according to claim 1 wherein the spinal facet fusion implant is asymmetric about the longitudinal axis of the elongated body.

11. A spinal facet fusion implant according to claim 10 wherein the elongated body is symmetrical about the longitudinal axis of the elongated body.

12. A spinal facet fusion implant according to claim 11 wherein the superior stabilizer and the inferior stabilizer have differing profiles in side view.

13. A spinal facet fusion implant according to claim 1 wherein the spinal facet fusion implant is symmetrical about the longitudinal axis of the elongated body.

14. A spinal facet fusion implant according to claim 1 wherein the distal end of the elongated body terminates in a distal end surface, wherein the elongated body comprises a beveled surface extending between the superior body surface and the distal end surface, and wherein the elongated body comprises a beveled surface extending between the inferior body surface and the distal end surface.

15. A spinal facet fusion implant according to claim 12 wherein the beveled surface extending between the superior body surface and the distal end surface extends at a first angle to the longitudinal axis of the elongated body, and the beveled surface extending between the inferior body surface and the distal end surface extends at a second angle to the longitudinal axis of the elongated body, and further wherein the first angle and the second angle are of the same size.

16. A spinal facet fusion implant according to claim 1 wherein the superior stabilizer comprises a beveled surface extending between the superior stabilizer and the superior body surface, and wherein the inferior stabilizer comprises a beveled surface extending between the inferior stabilizer and the inferior body surface.

17. A spinal facet fusion implant according to claim 16 wherein the beveled surface extending between the superior stabilizer and the superior body surface is disposed distal to the beveled surface extending between the inferior stabilizer and the inferior body surface.

18. A spinal facet fusion implant according to claim 1 wherein the superior stabilizer comprises two beveled surfaces extending between the superior stabilizer and the superior body surface, and wherein the inferior stabilizer comprises two beveled surfaces extending between the inferior stabilizer and the at least one inferior body surface.

19. A spinal facet fusion implant according to claim 18 wherein the two beveled surfaces extending between the superior stabilizer and the superior body surface extend at different angles to the longitudinal axis of the elongated body.

20. A spinal facet fusion implant according to claim 18 wherein the two beveled surfaces extending between the inferior stabilizer and the inferior body surface extend at different angles to the longitudinal axis of the elongated body.

21. A system for effecting spinal facet fusion, the system comprising:
   a spinal facet fusion implant comprising:
      an elongated body having a distal end, a proximal end and a longitudinal axis extending between the distal end and the proximal end, the elongated body being characterized by a superior body surface and an inferior body surface;
      a superior stabilizer extending outwardly from the superior body surface, the superior stabilizer being characterized by a superior stabilizer surface; and
      an inferior stabilizer extending outwardly from the inferior body surface, the inferior stabilizer being characterized by an inferior stabilizer surface;
      wherein (i) the superior body surface and the inferior body surface are tapered relative to one another, and/or (ii) the superior stabilizer surface and the inferior stabilizer surface are tapered relative to one another;
      wherein the elongated body comprises a proximal end surface, the superior stabilizer comprises a proximal end surface, and the inferior stabilizer comprises a proximal end surface, and further wherein the proximal end surface of the elongated body, the proximal end surface of the superior stabilizer, and the proximal end surface of the inferior stabilizer are all co-planar;
   a drill guide/cannula for preparing the anatomy to receive the spinal facet fusion implant and for delivering the spinal facet fusion implant to the anatomy, the drill guide/cannula comprising:
      a body having a distal end, a proximal end and a longitudinal axis extending therebetween, the distal end of the body being configured for engaging a gap between a descending facet of a first vertebra and an ascending facet of a second vertebra;
      a central lumen extending between the distal end of the body and the proximal end of the body, the central lumen having a cross-sectional profile which matches the cross-sectional profile of the spinal facet fusion implant such that the spinal facet fusion implant can be introduced into the proximal end of the central lumen, advanced distally along the central lumen, and advanced distally out of the distal end of the central lumen and into the gap between the descending facet of the first vertebra and the ascending facet of the second vertebra;
      a first drill guide angled relative to the longitudinal axis of the central lumen, the first drill guide being configured to receive a drill therein so as to drill a first seat in the descending facet of the first vertebra;
      a second drill guide angled relative to the longitudinal axis of the central lumen, the second drill guide being configured to receive a drill therein so as to drill a second seat in the ascending facet of the second vertebra;
      wherein the first seat in the descending facet of the first vertebra is sized and angled so as to receive the superior stabilizer of the spinal facet fusion implant when the spinal facet fusion implant is advanced into the gap between the first vertebra and the second vertebra; and
      wherein the second seat in the ascending facet of the second vertebra is sized and angled so as to receive the inferior stabilizer of the spinal facet fusion implant when the spinal facet fusion implant is advanced into the gap between the first vertebra and the second vertebra.

* * * * *